United States Patent
Zhelnin et al.

(10) Patent No.: US 6,927,041 B2
(45) Date of Patent: Aug. 9, 2005

(54) HUMAN NEUROPEPTIDE Y-LIKE G PROTEIN-COUPLED RECEPTOR

(75) Inventors: Leonid Zhelnin, Madison, CT (US); Brian T. Bloomquist, New Haven, CT (US)

(73) Assignee: Bayer Corporation, Pittsburgh, PA (US)

(*) Notice: Subject to any disclaimer, the term of this patent is extended or adjusted under 35 U.S.C. 154(b) by 339 days.

(21) Appl. No.: 09/899,532

(22) Filed: Jul. 6, 2001

(65) Prior Publication Data

US 2002/0048791 A1 Apr. 25, 2002

Related U.S. Application Data

(60) Provisional application No. 60/216,523, filed on Jul. 6, 2000.

(51) Int. Cl.[7] .......................... C07H 21/04; C12N 5/10; C12N 15/12; C12N 15/63; C12P 21/00
(52) U.S. Cl. .................. 435/69.1; 435/320.1; 435/325; 536/23.5
(58) Field of Search .............................. 435/69.1, 320.1, 435/325; 536/23.5

(56) References Cited

FOREIGN PATENT DOCUMENTS

| | | |
|---|---|---|
| EP | 1207201 | 5/2002 |
| WO | WO 00/11015 | 3/2000 |
| WO | WO 00/22131 | 4/2000 |
| WO | WO 00/31258 | 6/2000 |
| WO | WO 00/78809 | 12/2000 |

*Primary Examiner*—Michael Pak
*Assistant Examiner*—Stephen Gucker
(74) *Attorney, Agent, or Firm*—Banner & Witcoff, Ltd.

(57) ABSTRACT

Reagents which regulate human neuropeptide Y-like G protein-coupled receptor (NPY-like GPCR) protein and reagents which bind to human NPY-like GPCR gene products can play a role in preventing, ameliorating, or correcting dysfunctions or diseases including, but not limited to, obesity, diabetes, anxiety, hypertension, cocaine withdrawal, congestive heart failure, memory enhancement, cardiac and cerebral vasospasm, pheochromocytoma, ganglioneuroblastoma, Huntington's disease, Alzheimer's disease, and Parkinson's disease.

9 Claims, 4 Drawing Sheets

FIG. 1

```
 976 ATC TGT AAT CCC ATT GTC TAT GCA TTT ATG AAT GAA AAC TTC AAA AAA AAT GTT TTG TCT GCA GTT TGT TAT TGC 1050
 326  I   C   N   P   I   V   Y   A   F   M   N   E   N   F   K   K   N   V   L   S   A   V   C   Y   C   350

1051 ATA GTA AAT AAA ACC TTC TCT CCA GCA CAA AGG CAT GGA AAT TCA GGA ATT ACA ATG ATG CGG AAG AAA GCA AAG 1125
 351  I   V   N   K   T   F   S   P   A   Q   R   H   G   N   S   G   I   T   M   M   R   K   K   A   K   375

1126 TTT TCC CTC AGA GAG AAT CCA GTG GAG GAA ACC AAA GGA GAA GCA TTC AGT GAT GGC AAC ATT GAA GTC AAA TTG 1200
 376  F   S   L   R   E   N   P   V   E   E   T   K   G   E   A   F   S   D   G   N   I   E   V   K   L   400

1201 TGT GAA CAG ACA GAG GAG AAG AAA AAG CTC AAA CGA CAT CTT GCT CTC TTT AGG TCT GAA CTG GCT GAG AAT TCT 1275
 401  C   E   Q   T   E   E   K   K   K   L   K   R   H   L   A   L   F   R   S   E   L   A   E   N   S   425

1276 CCT TTA GAC AGT GAC GGG CAT TAA TTATAACAATATCTTCATAAT                                                1317
 426  P   L   D   S   D   G   H   *                                                                       432
```

Figure 1, cont.

SEQUENCE LISTING

<160> NUMBER OF SEQ ID NOS: 3

<210> SEQ ID NO 1
<211> LENGTH: 1296
<212> TYPE: DNA
<213> ORGANISM: Homo sapiens

<400> SEQUENCE: 1

| | | | | | |
|---|---|---|---|---|---|
| atgcaggcgc | ttaacattac | cccggagcag | ttctctcggc | tgctgcggga | ccacaacctg | 60 |
| acgcgggagc | agttcatcgc | tctgtaccgg | ctgcgaccgc | tcgtctacac | cccagagctg | 120 |
| ccgggacgcg | ccaagctggc | cctcgtgctc | accggcgtgc | tcatcttcgc | cctggcgctc | 180 |
| tttggcaatg | ctctggtgtt | ctacgtggtg | acccgcagca | aggccatgcg | caccgtcacc | 240 |
| aacatcttta | tctgctcctt | ggcgctcagt | gacctgctca | tcaccttctt | ctgcattccc | 300 |
| gtcaccatgc | tccagaacat | ttccgacaac | tggctggggg | gtgctttcat | ttgcaagatg | 360 |
| gtgccatttg | tccagtctac | cgctgttgtg | acagaaatcc | tcactatgac | ctgcattgct | 420 |
| gtggaaaggc | accagggact | tgtgcatcct | tttaaaatga | agtggcaata | caccaaccga | 480 |
| agggctttca | caatgctagg | tgtggtctgg | ctggtggcag | tcatcgtagg | atcacccatg | 540 |
| tggcacgtgc | aacaacttga | gatcaaatat | gacttcctat | atgaaaagga | acacatctgc | 600 |
| tgcttagaag | agtggaccag | ccctgtgcac | cagaagatct | acaccacctt | catccttgtc | 660 |
| atcctcttcc | tcctgcctct | tatggtgatg | cttattctgt | acagtaaaat | tggttatgaa | 720 |
| ctttggataa | agaaaagagt | tggggatggt | tcagtgcttc | gaactattca | tggaaaagaa | 780 |
| atgtccaaaa | tagccaggaa | gaagaaacga | gctgtcatta | tgatggtgac | agtggtggct | 840 |
| ctctttgctg | tgtgctgggc | accattccat | gttgtccata | tgatgattga | atacagtaat | 900 |
| tttgaaaagg | aatatgatga | tgtcacaatc | aagatgattt | ttgctatcgt | gcaaattatt | 960 |
| ggattttcca | actccatctg | taatcccatt | gtctatgcat | ttatgaatga | aaacttcaaa | 1020 |
| aaaaatgttt | tgtctgcagt | ttgttattgc | atagtaaata | aaccttctc | tccagcacaa | 1080 |
| aggcatggaa | attcaggaat | tacaatgatg | cggaagaaag | caagttttc | cctcagagag | 1140 |
| aatccagtgg | aggaaaccaa | aggagaagca | ttcagtgatg | gcaacattga | agtcaaattg | 1200 |
| tgtgaacaga | cagaggagaa | gaaaaagctc | aaacgacatc | ttgctctctt | taggtctgaa | 1260 |
| ctggctgaga | attctccttt | agacagtggg | cattaa | | | 1296 |

<210> SEQ ID NO 2
<211> LENGTH: 431
<212> TYPE: PRT
<213> ORGANISM: Homo sapiens

<400> SEQUENCE: 2

Met Gln Ala Leu Asn Ile Thr Pro Glu Gln Phe Ser Arg Leu Leu Arg
 1               5                  10                  15

Asp His Asn Leu Thr Arg Glu Gln Phe Ile Ala Leu Tyr Arg Leu Arg
            20                  25                  30

Pro Leu Val Tyr Thr Pro Glu Leu Pro Gly Arg Ala Lys Leu Ala Leu
        35                  40                  45

Val Leu Thr Gly Val Leu Ile Phe Ala Leu Ala Leu Phe Gly Asn Ala
    50                  55                  60

Leu Val Phe Tyr Val Val Thr Arg Ser Lys Ala Met Arg Thr Val Thr
65                  70                  75                  80

```
Asn Ile Phe Ile Cys Ser Leu Ala Leu Ser Asp Leu Ile Thr Phe
                85                  90                  95
Phe Cys Ile Pro Val Thr Met Leu Gln Asn Ile Ser Asp Asn Trp Leu
                100                 105                 110
Gly Gly Ala Phe Ile Cys Lys Met Val Pro Phe Val Gln Ser Thr Ala
                115                 120                 125
Val Val Thr Glu Ile Leu Thr Met Thr Cys Ile Ala Val Glu Arg His
    130                 135                 140
Gln Gly Leu Val His Pro Phe Lys Met Lys Trp Gln Tyr Thr Asn Arg
145                 150                 155                 160
Arg Ala Phe Thr Met Leu Gly Val Val Trp Leu Val Ala Val Ile Val
                165                 170                 175
Gly Ser Pro Met Trp His Val Gln Gln Leu Glu Ile Lys Tyr Asp Phe
                180                 185                 190
Leu Tyr Glu Lys Glu His Ile Cys Cys Leu Glu Glu Trp Thr Ser Pro
        195                 200                 205
Val His Gln Lys Ile Tyr Thr Thr Phe Ile Leu Val Ile Leu Phe Leu
    210                 215                 220
Leu Pro Leu Met Val Met Leu Ile Leu Tyr Ser Lys Ile Gly Tyr Glu
225                 230                 235                 240
Leu Trp Ile Lys Lys Arg Val Gly Asp Gly Ser Val Leu Arg Thr Ile
                245                 250                 255
His Gly Lys Glu Met Ser Lys Ile Ala Arg Lys Lys Arg Ala Val
                260                 265                 270
Ile Met Met Val Thr Val Val Ala Leu Phe Ala Val Cys Trp Ala Pro
                275                 280                 285
Phe His Val Val His Met Met Ile Glu Tyr Ser Asn Phe Glu Lys Glu
    290                 295                 300
Tyr Asp Asp Val Thr Ile Lys Met Ile Phe Ala Ile Val Gln Ile Ile
305                 310                 315                 320
Gly Phe Ser Asn Ser Ile Cys Asn Pro Ile Val Tyr Ala Phe Met Asn
                325                 330                 335
Glu Asn Phe Lys Lys Asn Val Leu Ser Ala Val Cys Tyr Cys Ile Val
                340                 345                 350
Asn Lys Thr Phe Ser Pro Ala Gln Arg His Gly Asn Ser Gly Ile Thr
                355                 360                 365
Met Met Arg Lys Lys Ala Lys Phe Ser Leu Arg Glu Asn Pro Val Glu
    370                 375                 380
Glu Thr Lys Gly Glu Ala Phe Ser Asp Gly Asn Ile Glu Val Lys Leu
385                 390                 395                 400
Cys Glu Gln Thr Glu Lys Lys Lys Leu Lys Arg His Leu Ala Leu
                405                 410                 415
Phe Arg Ser Glu Leu Ala Glu Asn Ser Pro Leu Asp Ser Gly His
                420                 425                 430
```

<210> SEQ ID NO 3
<211> LENGTH: 1710
<212> TYPE: DNA
<213> ORGANISM: Homo sapiens

<400> SEQUENCE: 3

```
tggccctcga ggccaagaat tcggcacgag gaggcgggga gccagaggcg ccaggaccct    60
cgcgtggcgc tccagcaccc cagaccgtgg cggcgcctcg ccttagggaa gagcaaggga   120
agaactttat ttgaaccgcg aacatttttt ggtcactgag atcgagtctc ccagtgcttt   180
```

-continued

```
ggcttcccgc ctctttatcg tgggtttgat ccctgagctg ctctcctttc ccgaacctcc    240
cggggtgcag cctagagccc tcccgcgcgg ctgactccag agtagaggaa gggaggcggc    300
ctccggctgg tcccccgaag ccctcgctgc ccgcagatg cggatggcca gccagtagcg     360
ggcggtggcc ccgcgtcccg ggagcgcaca gcaatgcagg cgcttaacat taccccggag    420
cagttctctc ggctgctgcg ggaccacaac ctgacgcggg agcagttcat cgctctgtac    480
cggctgcgac cgctcgtcta cacccagag ctgccgggac gcgccaagct ggccctcgtg     540
ctcaccggcg tgctcatctt cgccctggcg ctctttggca atgctctggt gttctacgtg    600
gtgacccgca gcaaggccat gcgcaccgtc accaacatct ttatctgctc cttggcgctc    660
agtgacctgc tcatcacctt cttctgcatt cccgtcacca tgctccagaa catttccgac    720
aactggctgg ggggtgcttt catttgcaag atggtgccat ttgtccagtc taccgctgtt    780
gtgacagaaa tcctcactat gacctgcatt gctgtggaaa ggcaccaggg acttgtgcat    840
ccttttaaaa tgaagtggca atacaccaac cgaagggctt tcacaatgct aggtgtggtc    900
tggctggtgg cagtcatcgt aggatcaccc atgtggcacg tgcaacaact tgagatcaaa    960
tatgacttcc tatatgaaaa ggaacacatc tgctgcttag aagagtggac cagccctgtg   1020
caccagaaga tctacaccac cttcatcctt gtcatcctct tcctcctgcc tcttatggtg   1080
atgcttattc tgtacagtaa aattggttat gaactttgga taaagaaaag agttggggat   1140
ggttcagtgc ttcgaactat tcatggaaaa gaaatgtcca aaatagccag gaagaagaaa   1200
cgagctgtca ttatgatggt gacagtggtg gctctctttg ctgtgtgctg ggcaccattc   1260
catgttgtcc atatgatgat tgaatacagt aattttgaaa aggaatatga tgatgtcaca   1320
atcaagatga tttttgctat cgtgcaaatt attggatttt ccaactccat ctgtaatccc   1380
attgtctatg catttatgaa tgaaaacttc aaaaaaaatg ttttgtctgc agtttgttat   1440
tgcatagtaa ataaaacctt ctctccagca caaaggcatg gaaattcagg aattacaatg   1500
atgcggaaga aagcaaagtt ttccctcaga gagaatccag tggaggaaac caaaggagaa   1560
gcattcagtg atggcaacat tgaagtcaaa ttgtgtgaac agacagagga gaagaaaaag   1620
ctcaaacgac atcttgctct ctttaggtct gaactggctg agaattctcc tttagacagt   1680
gggcattaat tataacaata tcttcataat                                   1710
```

HUMAN NEUROPEPTIDE Y-LIKE G PROTEIN-COUPLED RECEPTOR

This application incorporates by reference and claims the benefit of now abandoned provisional application Ser. No. 60/216,523 filed Jul. 6, 2000.

TECHNICAL FIELD OF THE INVENTION

The invention relates to the area of G-protein coupled receptors. More particularly, it relates to the area of human neuropeptide Y-like G protein-coupled receptor and its regulation.

BACKGROUND OF THE INVENTION

G-Protein Coupled Receptors

Many medically significant biological processes are mediated by signal transduction pathways that involve G-proteins (Lefkowitz, Nature 351, 353–354, 1991). The family of G-protein coupled receptors (GPCR) includes receptors for hormones, neurotransmitters, growth factors, and viruses. Specific examples of GPCRs include receptors for such diverse agents as dopamine, calcitonin, adrenergic hormones, endothelin, cAMP, adenosine, acetylcholine, serotonin, histamine, thrombin, kinin, follicle stimulating hormone, opsins, endothelial differentiation gene-1, rhodopsins, odorants, cytomegalovirus, G-proteins themselves, effector proteins such as phospholipase C, adenyl cyclase, and phosphodiesterase, and actuator proteins such as protein kinase A and protein kinase C.

GPCRs possess seven conserved membrane-spanning domains connecting at least eight divergent hydrophilic loops. GPCRs (also known as 7TM receptors) have been characterized as including these seven conserved hydrophobic stretches of about 20 to 30 amino acids, connecting at least eight divergent hydrophilic loops. Most GPCRs have single conserved cysteine residues in each of the first two extracellular loops, which form disulfide bonds that are believed to stabilize functional protein structure. The seven transmembrane regions are designated as TM1, TM2, TM3, TM4, TM5, TM6, and TM7. TM3 has been implicated in signal transduction.

Phosphorylation and lipidation (palmitylation or farnesylation) of cysteine residues can influence signal transduction of some GPCRs. Most GPCRs contain potential phosphorylation sites within the third cytoplasmic loop and/or the carboxy terminus. For several GPCRs, such as the •-adrenergic receptor, phosphorylation by protein kinase A and/or specific receptor kinases mediates receptor desensitization.

For some receptors, the ligand binding sites of GPCRs are believed to comprise hydrophilic sockets formed by several GPCR transmembrane domains. The hydrophilic sockets are surrounded by hydrophobic residues of the GPCRs. The hydrophilic side of each GPCR transmembrane helix is postulated to face inward and form a polar ligand binding site. TM3 has been implicated in several GPCRs as having a ligand binding site, such as the TM3 aspartate residue. TM5 serines, a TM6 asparagine, and TM6 or TM7 phenylalanines or tyrosines also are implicated in ligand binding.

GPCRs are coupled inside the cell by heterotrimeric G-proteins to various intracellular enzymes, ion channels, and transporters (see Johnson et al., Endoc. Rev. 10, 317–331, 1989). Different G-protein alpha-subunits preferentially stimulate particular effectors to modulate various biological functions in a cell. Phosphorylation of cytoplasmic residues of GPCRs is an important mechanism for the regulation of some GPCRs. For example, in one form of signal transduction, the effect of hormone binding is the activation inside the cell of the enzyme, adenylate cyclase. Enzyme activation by hormones is dependent on the presence of the nucleotide GTP. GTP also influences hormone binding. A G-protein connects the hormone receptor to adenylate cyclase. G-protein exchanges GTP for bound GDP when activated by a hormone receptor. The GTP-carrying form then binds to activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

Over the past 15 years, nearly 350 therapeutic agents targeting GPCRs receptors have been successfully introduced onto the market. This indicates that these receptors have an established, proven history as therapeutic targets. Clearly, there is an on-going need for identification and characterization of further GPCRs which can play a role in preventing, ameliorating, or correcting dysfunctions or diseases including, but not limited to, infections such as bacterial, fungal, protozoan, and viral infections, particularly those caused by HIV viruses, pain, cancers, anorexia, bulimia, asthma, Parkinson's diseases, acute heart failure, hypotension, hypertension, urinary retention, osteoporosis, angina pectoris, myocardial infarction, ulcers, asthma, allergies, benign prostatic hypertrophy, and psychotic and neurological disorders, including anxiety, schizophrenia, manic depression, delirium, dementia, several mental retardation, and dyskinesias, such as Huntington's disease and Tourett's syndrome.

Neuropeptide Y

Neuropeptide Y (NPY) is a 36-residue, amidated polypeptide. It is anatomically co-distributed and co-released with norepinephrine in and from sympathetic postganglionic neurons (11, 2, 3, 4, 5, and 6). Stimulation of the sympathetic nervous system under physiological circumstances such as exercise (7, 8) or exposure to the cold (9, 10) promotes an elevation of both norepinephrine and NPY.

NPY is believed to act in the regulation of appetite control (11, 12) and vascular smooth muscle tone (13, 14), as well as regulation of blood pressure (6, 15, 16, 17). NPY also decreases cardiac contractility (18, 19, 20, 21, 22). Congestive heart failure and cardiogenic shock are associated with probable releases of NPY into the blood (23, 24, 25). Regulation of NPY levels may be beneficial to these disease states (26).

At the cellular level, NPY binds to a G-protein coupled receptor (GPCR) (27, 28, 29, 30). NPY is involved in regulating eating behavior and is an extremely potent orixigenic agent (11, 12, 31). When administered intracerebroventricularly or injected into the hypothalamic paraventricular nucleus (PVN) it elicits eating in satiated rats (32, 33, 34) and intraventricular injection of antisera to NPY decreases eating (11, 31). It has been shown to stimulate appetite in a variety of species and at different stages of development (12). Other effects on energy metabolism include decreased thermogenesis, body temperature, and uncoupling protein, and increased white fat storage and lipoprotein lipase activity (9, 35, 36, 37, 38, 39). NPY levels in the PVN increase upon fasting (40, 41, 42, 43, 44), before a scheduled meal (31, 36, 40), and in both streptozotocin-induced and spontaneous diabetes (36, 45, 46, 47, 48, 49). Also, NPY levels are increased in genetically obese and hyperphagic Zucker rats (36, 50, 51). Thus, a specific centrally acting antagonist for the appropriate NPY receptor subtype may be therapeutically useful for treating obesity and diabetes. Other disorders which can be targeted therapeutically include anxiety, hypertension, cocaine withdrawal, congestive heart failure, memory enhancement, cardiac and cerebral vasospasm, pheochromocytoma and ganglioneuroblastoma, and Huntington's, Alzheimer's, and Parkinson's diseases (26, 52).

Neuropeptide Y Receptors

At least four receptor subtypes of the NPY family have been proposed based on pharmacological and physiological properties. The Y1 receptor is stimulated by NPY or PYY (peptide YY) and appears to be the major vascular receptor (16, 53, 54, 55). The Y2 receptor is stimulated by C-terminal fragments of NPY or PYY and is abundantly expressed both centrally and peripherally (55, 56, 57, 58). A third receptor (Y3) is exclusively responsive to NPY and is likely present in adrenal medulla, heart, and brainstem (27, 59). In addition, other subtypes of this receptor family are known to exist, based on pharmacological and physiological characterization (60, 61, 62, 63). The feeding behavior is stimulated potently by NPY, $NPY_{2-36}$, and the $Y_1$ agonist Leu31, Pro34 NPY, but is not stimulated by the Y2 agonist $NPY_{13-36}$ (11, 64, 65, 66). This pharmacology is not characteristic of the defined Y1, Y2, or Y3 receptors and can thus be attributed to a unique receptor, termed "atypical Y1" (11, 65, 66), which is responsible for evoking the feeding response. In addition, data indicate the existence of additional members of this receptor family, including one subtype specific for peptide PP (62, 63), one with affinity for short C-terminal fragments of NPY which induce hypotension when administered systemically (15, 17, 30, 67, 68), and one associated with binding of NPY and PYY to brain sigma and phencyclidine binding sites (61).

The Y1 receptor has been cloned and shown to be a G-protein coupled receptor (53, 69, 70). Recently, the Y2 receptor has been cloned (71, 72). In addition, a peptide PP-preferring receptor, termed PPI (73) or Y4 (74), has been cloned. Other NPY receptors also have been recently identified and cloned. See U.S. Pat. Nos. 5,939,263 and 5,965,392.

Because of the diverse biological effects of neuropeptide Y receptors, there is a need in the art to identify additional members of the neuropeptide Y receptor family whose activity can be regulated to provide therapeutic effects.

SUMMARY OF THE INVENTION

It is an object of the invention to provide reagents and methods of regulating a human neuropeptide Y-like G protein-coupled receptor protein. This and other objects of the invention are provided by one or more of the embodiments described below.

One embodiment of the invention is an isolated polynucleotide encoding a polypeptide that comprises the amino acid sequence shown in SEQ ID NO:2.

Another embodiment of the invention is an expression vector comprising a polynucleotide that encodes a polypeptide comprising the amino acid sequence shown in SEQ ID NO:2.

Still another embodiment of the invention is a host cell comprising an expression vector comprising a polynucleotide that encodes a polypeptide comprising the amino acid sequence shown in SEQ ID NO:2.

Even another embodiment of the invention is a purified polypeptide comprising the amino acid sequence shown in SEQ ID NO:2.

Yet another embodiment of the invention is a fusion protein comprising a polypeptide consisting of the amino acid sequence shown in SEQ ID NO:2.

A further embodiment of the invention is a method of producing a polypeptide comprising the amino acid sequence shown in SEQ ID NO:2. A host cell comprising an expression vector that comprising the nucleotide sequence shown in SEQ ID NO:1 is cultured under conditions whereby the polypeptide is expressed. The polypeptide is isolated.

Another embodiment of the invention is a method of detecting a coding sequence for a polypeptide comprising the amino acid sequence shown in SEQ ID NO:2. A polynucleotide is hybridized to nucleic acid material of a biological sample, thereby forming a hybridization complex. The polynucleotide comprises 11 contiguous nucleotides of the complement of the nucleotide sequence shown in SEQ ID NO:1. The hybridization complex is detected.

Still another embodiment of the invention is a kit for detecting a coding sequence for a polypeptide comprising the amino acid sequence shown in SEQ ID NO:2. The kit comprises a polynucleotide comprising 11 contiguous nucleotides of the complement of the nucleotide sequence shown in SEQ ID NO:1 and instructions for detecting the coding sequence.

Even another embodiment of the invention is a method of detecting a polypeptide comprising the amino acid sequence shown in SEQ ID NO:2. A biological sample is contacted with an antibody that specifically binds to the polypeptide to form a reagent-polypeptide complex. The reagent-polypeptide complex is detected.

Yet another embodiment of the invention is a kit for detecting a polypeptide comprising the amino acid sequence shown in SEQ ID NO:2. The kit comprises an antibody that specifically binds to the polypeptide and instructions for detecting the polypeptide.

A further embodiment of the invention is a method of screening for agents that can regulate the activity of a neuropeptide Y-like G protein-coupled receptor (NPY-like GPCR). A test compound is contacted with a polypeptide comprising the amino acid sequence shown in SEQ ID NO:2. Binding of the test compound to the polypeptide is detected. A test compound that binds to the polypeptide is identified as a potential agent for regulating activity of the NPY-like GPCR.

Another embodiment of the invention is a method of screening for agents that can regulate the activity of an NPY-like GPCR. A test compound is contacted with a product encoded by a polynucleotide comprising the nucleotide sequence shown in SEQ ID NO:1. Binding of the test compound to the product is detected. A test compound that binds to the product is thereby identified as a potential agent for regulating the activity of the NPY-like GPCR.

Even another embodiment of the invention is a method of reducing expression of an NPY-like GPCR. A cell is contacted with an antibody that specifically binds to a polypeptide comprising the amino acid sequence shown in SEQ ID NO:2. Expression of the NPY-like GPCR is thereby reduced.

Still another embodiment of the invention is a method of reducing expression of an NPY-like GPCR. A cell is contacted with an antisense oligonucleotide that specifically binds to a the nucleotide sequence shown in SEQ ID NO:1. Expression of the NPY-like GPCR is thereby reduced.

A further embodiment of the invention is a pharmaceutical composition comprising an antibody that specifically binds to a polypeptide comprising the amino acid sequence shown in SEQ ID NO:2 and a pharmaceutically acceptable carrier.

Yet another embodiment of the invention is a pharmaceutical composition comprising an antisense oligonucleotide that specifically binds to the nucleotide sequence shown in SEQ ID NO:1 and a pharmaceutically acceptable carrier.

Another embodiment of the invention is a pharmaceutical composition comprising an expression vector encoding a polypeptide comprising the amino acid sequence shown in SEQ ID NO:2 and a pharmaceutically acceptable carrier.

Still another embodiment of the invention is a method of treating obesity. A therapeutically effective dose of a reagent that regulates expression of the NPY-like GPCR is administered to a patient in need thereof. Symptoms of the obesity are thereby ameliorated.

Yet another embodiment of the invention is an antibody that specifically binds to a polypeptide comprising the amino acid sequence shown in SEQ ID NO:2.

The invention thus provides a human neuropeptide Y-like G protein-coupled receptor that can be used to identify test compounds that may act as agonists or antagonists at the receptor site. Human neuropeptide Y-like G protein-coupled receptor and fragments thereof also are useful in raising specific antibodies that can block the receptor and effectively prevent ligand binding.

BRIEF DESCRIPTION OF THE DRAWINGS

Figure 1:
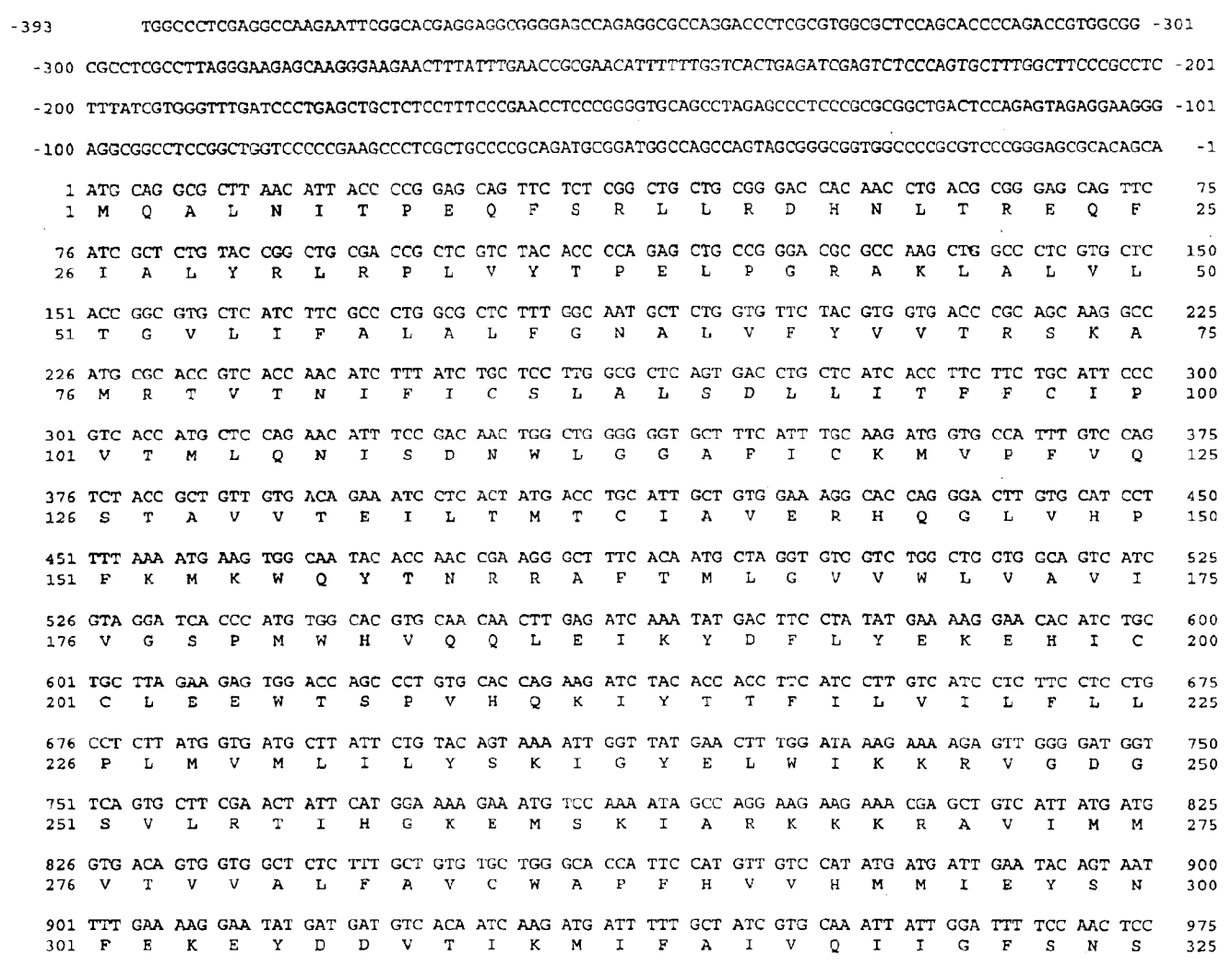

FIG. 1. Nucleotide and deduced amino acid sequences of the human orphan NPY-like GPCR. The nucleotide (above; SEQ ID NO:1) and amino acid (below; SEQ ID NO:2) positions are indicated on the right and left. The STOP codon is indicated with an asterisk.

DETAILED DESCRIPTION OF THE INVENTION

Figure 2:
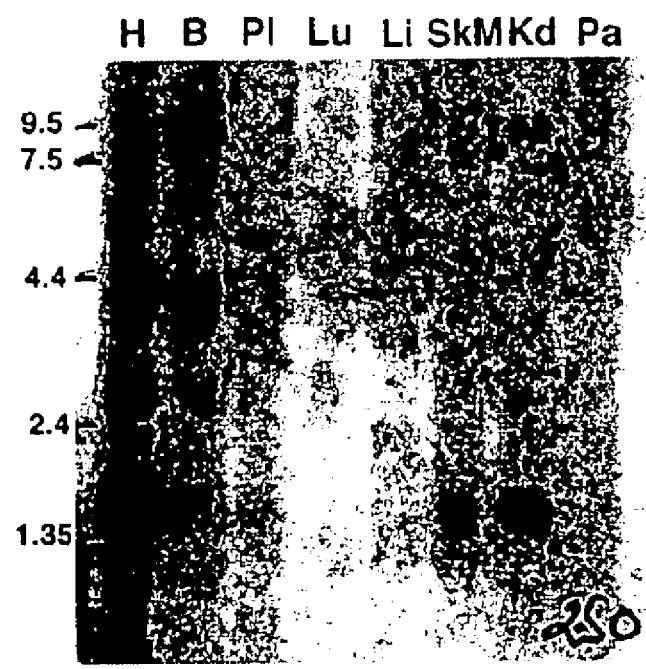
FIG. 2. Expression profile of the NPY-like GPCR in human tissues.

A novel human neuropeptide Y-like GPCR (NPY-like GPCR) is a discovery of the present invention. NPY-like GPCR is most highly expressed in human brain and heart and has the highest homology to NPY and orexin receptors. The amino acid sequence of the receptor is shown in SEQ ID NO:2; a coding sequence for the receptor is shown in SEQ ID NO:1. This sequence is contained within the longer sequence shown in SEQ ID NO:3.

The endogenous ligand for human NPY-like GPCR is not known. Neuropeptide Y, peptide YY, pancreatic polypeptide, orexin-A, and galanin do not appear to have binding affinity for the receptor. However, based on its homology with known receptors, human NPY-like GPCR is expected to be useful for the same purposes as previously identified neuropeptide Y receptors. Thus, NPY-like GPCR protein can be used in therapeutic methods to treat disorders such as obesity, bacterial, fungal, protozoan, and viral infections, particularly those caused by HIV viruses, pain, cancers, anorexia, bulimia, diabetes, asthma, Parkinson's diseases, acute heart failure, hypotension, hypertension, urinary retention, osteoporosis, angina pectoris, myocardial infarction, ulcers, asthma, allergies, benign prostatic hypertrophy, and psychotic and neurological disorders, including anxiety, schizophrenia, manic depression, delirium, dementia, several mental retardation, and dyskinesias, such as Huntington's disease and Tourett's syndrome. Human NPY-like GPCR protein also can be used to screen for NPY-like GPCR agonists and antagonists.

Polypeptides

NPY-like GPCR polypeptides according to the invention comprise at least 10, 15, 25, 50, 75, 100, 125, 150, 175, 200, 225, 250, 275, 300, 325, 350, 375, 400, 425, or 430 contiguous amino acids selected from SEQ ID NO:2 or from a biologically active variant thereof, as defined below. An NPY-like GPCR polypeptide of the invention therefore can be a portion of an NPY-like GPCR protein, a full-length NPY-like GPCR protein, or a fusion protein comprising all or a portion of an NPY-like GPCR protein.

Biologically Active Variants

NPY-like GPCR polypeptide variants which are biologically active, i.e., retain the ability to bind a ligand to produce a biological effect, such as cyclic AMP formation, mobilization of intracellular calcium, or phosphoinositide metabolism, also are NPY-like GPCR polypeptides. Peptides that do not appear to have binding affinity for the receptor include NPY, peptide YY, pancreatic polypeptide, orexin-A, and galanin. Preferably, naturally or non-naturally occurring NPY-like GPCR polypeptide variants have amino acid sequences which are at least about 50, 55, 60, 65, 70, preferably about 75, 90, 96, or 98% identical to an amino acid sequence shown in SEQ ID NO:2 or a fragment thereof. Percent identity between a putative NPY-like GPCR polypeptide variant and an amino acid sequence of SEQ ID NO:2 is determined using the Blast2 alignment program (Blosum62, expect 10, standard genetic codes).

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of an NPY-like GPCR polypeptide can be found using computer programs well known in the art, such as DNASTAR software. Whether an amino acid change results in a biologically active NPY-like GPCR polypeptide can readily be determined by assaying for binding to a ligand or by conducting a functional assay, as described for example, in the specific Examples, below.

Fusion Proteins

Fusion proteins are useful for generating antibodies against NPY-like GPCR polypeptide amino acid sequences and for use in various assay systems. For example, fusion proteins can be used to identify proteins that interact with portions of an NPY-like GPCR polypeptide. Protein affinity chromatography or library-based assays for protein-protein interactions, such as the yeast two-hybrid or phage display systems, can be used for this purpose. Such methods are well known in the art and also can be used as drug screens.

An NPY-like GPCR polypeptide fusion protein comprises two polypeptide segments fused together by means of a peptide bond. The first polypeptide segment comprises at least 10, 15, 25, 50, 75, 100, 125, 150, 175, 200, 225, 250, 275, 300, 325, 350, 375, 400, 425, or 430 or more contiguous amino acids of SEQ ID NO:2 or from a biologically active variant, such as those described above. The first polypeptide segment also can comprise full-length NPY-like GPCR protein.

The second polypeptide segment can be a full-length protein or a protein fragment. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions. A fusion protein also can be engineered to contain a cleavage site located between the NPY-like GPCR polypeptide-encoding sequence and the heterologous protein sequence, so that the NPY-like GPCR polypeptide can be cleaved and purified away from the heterologous moiety.

A fusion protein can be synthesized chemically, as is known in the art. Preferably, a fusion protein is produced by covalently linking two polypeptide segments or by standard procedures in the art of molecular biology. Recombinant DNA methods can be used to prepare fusion proteins, for example, by making a DNA construct which comprises coding sequences selected from SEQ ID NO:1 in proper reading frame with nucleotides encoding the second polypeptide segment and expressing the DNA construct in a host cell, as is known in the art. Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Identification of Species Homologs

Species homologs of human NPY-like GPCR polypeptide can be obtained using NPY-like GPCR polypeptide polynucleotides (described below) to make suitable probes or primers for screening cDNA expression libraries from other species, such as mice, monkeys, or yeast, identifying cDNAs which encode homologs of NPY-like GPCR polypeptide, and expressing the cDNAs as is known in the art.

Polynucleotides

An NPY-like GPCR polynucleotide can be single- or double-stranded and comprises a coding sequence or the complement of a coding sequence for an NPY-like GPCR polypeptide. A coding sequence for human NPY-like GPCR is shown in SEQ ID NO:1. The gene encoding NPY-like GPCR is located at chromosome 11q12.2; the location of SEQ ID NO:1 within the genomic sequence is indicated in SEQ ID NO:3.

Degenerate nucleotide sequences encoding human NPY-like GPCR polypeptides, as well as homologous nucleotide sequences which are at least about 50, 55, 60, 65, 70, preferably about 75, 90, 96, or 98% identical to the nucleotide sequence shown in SEQ ID NO:1 also are NPY-like GPCR polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of NPY-like GPCR polynucleotides which encode biologically active NPY-like GPCR polypeptides also are NPY-like GPCR polynucleotides.

Identification of Polynucleotide Variants and Homologs

Variants and homologs of the NPY-like GPCR polynucleotides described above also are NPY-like GPCR polynucleotides. Typically, homologous NPY-like GPCR polynucleotide sequences can be identified by hybridization of candidate polynucleotides to known NPY-like GPCR polynucleotides under stringent conditions, as is known in the art. For example, using the following wash conditions—2× SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each-homologous sequences can be identified which contain at most about 25–30% basepair mismatches. More preferably, homologous nucleic acid strands contain 15–25% basepair mismatches, even more preferably 5–15% basepair mismatches.

Species homologs of the NPY-like GPCR polynucleotides disclosed herein also can be identified by making suitable probes or primers and screening cDNA expression libraries from other species, such as mice, monkeys, or yeast. Human variants of NPY-like GPCR polynucleotides can be identified, for example, by screening human cDNA expression libraries. It is well known that the $T_m$ of a double-stranded DNA decreases by 1–1.5° C. with every 1% decrease in homology (Bonner et al., *J. Mol. Biol.* 81, 123 (1973). Variants of human NPY-like GPCR polynucleotides or NPY-like GPCR polynucleotides of other species can therefore be identified by hybridizing a putative homologous NPY-like GPCR polynucleotide with a polynucleotide having a nucleotide sequence of SEQ ID NO:1 or the complement thereof to form a test hybrid. The melting temperature of the test hybrid is compared with the melting temperature of a hybrid comprising NPY-like GPCR polynucleotides having perfectly complementary nucleotide sequences, and the number or percent of basepair mismatches within the test hybrid is calculated.

Nucleotide sequences which hybridize to NPY-like GPCR polypeptides or their complements following stringent hybridization and/or wash conditions also are NPY-like GPCR polynucleotides. Stringent wash conditions are well known and understood in the art and are disclosed, for example, in Sambrook et al., MOLECULAR CLONING: A LABORATORY MANUAL, 2d ed., 1989, at pages 9.50–9.51.

Typically, for stringent hybridization conditions a combination of temperature and salt concentration should be chosen that is approximately 12–20° C. below the calculated $T_m$ of the hybrid under study. The $T_m$ of a hybrid between an NPY-like GPCR polynucleotide having a nucleotide sequence shown in SEQ ID NO:1 or the complement thereof and a polynucleotide sequence which is at least about 50, 55, 60, 65, 70, preferably about 75, 90, 96, or 98% identical to one of those nucleotide sequences can be calculated, for example, using the equation of Bolton and McCarthy, *Proc. Natl. Acad. Sci. U.S.A.* 48, 1390 (1962):

$$T_m = 81.5° C. - 16.6(\log_{10}[Na^+]) + 0.41(\% \ G+C) - 0.63(\% \ \text{formamide}) - 600/l),$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

Preparation of Polynucleotides

An NPY-like GPCR polynucleotide can be isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated NPY-like GPCR polynucleotides. For example, restriction enzymes and probes can be used to isolate polynucleotide fragments that comprise NPY-like GPCR nucleotide sequences. Isolated polynucleotides are in preparations that are free or at least 70, 80, or 90% free of other molecules.

NPY-like GPCR cDNA molecules can be made with standard molecular biology techniques, using NPY-like GPCR mRNA as a template. NPY-like GPCR cDNA molecules can thereafter be replicated using molecular biology techniques known in the art and disclosed in manuals such as Sambrook et al. (1989). An amplification technique, such as PCR, can be used to obtain additional copies of polynucleotides of the invention, using either human genomic DNA or cDNA as a template.

Alternatively, synthetic chemistry techniques can be used to synthesize NPY-like GPCR polynucleotides. The degeneracy of the genetic code allows alternate nucleotide sequences to be synthesized which will encode an NPY-like GPCR polypeptide having, for example, an amino acid sequence shown in SEQ ID NO:2 or a biologically active variant thereof.

Extending NPY-like GPCR Polynucleotides

Various PCR-based methods can be used to extend the nucleic acid sequences encoding the disclosed portions of human NPY-like GPCR polypeptide to detect upstream sequences such as promoters and regulatory elements. For example, restriction-site PCR uses universal primers to retrieve unknown sequence adjacent to a known locus (Sarkar, *PCR Methods Applic.* 2, 318–322, 1993). Genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR also can be used to amplify or extend sequences using divergent primers based on a known region (Triglia et al., *Nucleic Acids Res.* 16, 8186, 1988). Primers can be designed using commercially available software, such as OLIGO 4.06 Primer Analysis software (National Biosciences Inc., Plymouth, Minn.), to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template.

Another method which can be used is capture PCR, which involves PCR amplification of DNA fragments adjacent to a known sequence in human and yeast artificial chromosome DNA (Lagerstrom et al., *PCR Methods Applic.* 1, 111–119, 1991). In this method, multiple restriction enzyme digestions and ligations also can be used to place an engineered double-stranded sequence into an unknown fragment of the DNA molecule before performing PCR.

Another method which can be used to retrieve unknown sequences is that of Parker et al., *Nucleic Acids Res.* 19, 3055–3060, 1991). Additionally, PCR, nested primers, and PROMOTERFINDER libraries (CLONTECH, Palo Alto, Calif.) can be used to walk genomic DNA (CLONTECH, Palo Alto, Calif.). This process avoids the need to screen libraries and is useful in finding intron/exon junctions.

When screening for full-length cDNAs, it is preferable to use libraries that have been size-selected to include larger cDNAs. Randomly-primed libraries are preferable, in that they will contain more sequences which contain the 5' regions of genes. Use of a randomly primed library may be especially preferable for situations in which an oligo d(T) library does not yield a full-length cDNA. Genomic libraries can be useful for extension of sequence into 5' non-transcribed regulatory regions.

Commercially available capillary electrophoresis systems can be used to analyze the size or confirm the nucleotide sequence of PCR or sequencing products. For example, capillary sequencing can employ flowable polymers for electrophoretic separation, four different fluorescent dyes (one for each nucleotide) that are laser activated, and detection of the emitted wavelengths by a charge coupled device camera. Output/light intensity can be converted to electrical signal using appropriate software (e.g. GENOTYPER and Sequence NAVIGATOR, Perkin Elmer), and the entire process from loading of samples to computer analysis and electronic data display can be computer controlled. Capillary electrophoresis is especially preferable for the sequencing of small pieces of DNA that might be present in limited amounts in a particular sample.

Obtaining NPY-like GPCR Polypeptides

NPY-like GPCR polypeptides can be obtained, for example, by purification from host cells, by expression of NPY-like GPCR polynucleotides, or by direct chemical synthesis.

Protein Purification

NPY-like GPCR polypeptides can be purified from any cell that expresses the receptor, including host cells that have been transfected with NPY-like GPCR polynucleotides. Kidney tumors and prostate are particularly useful sources of NPY-like GPCR polypeptides. A purified NPY-like GPCR polypeptide is separated from other compounds that normally associate with the NPY-like GPCR polypeptide in the cell, such as certain proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis.

NPY-like GPCR polypeptide can be conveniently isolated as a complex with its associated G protein, as described in the specific examples, below. A preparation of purified NPY-like GPCR polypeptides is at least 80% pure; preferably, the preparations are 90%, 95%, or 99% pure. Purity of the preparations can be assessed by any means known in the art, such as SDS-polyacrylamide gel electrophoresis.

Expression of NPY-like GPCR Polynucleotides

To express an NPY-like GPCR polypeptide, an NPY-like GPCR polynucleotide can be inserted into an expression vector that contains the necessary elements for the transcription and translation of the inserted coding sequence. Methods that are well known to those skilled in the art can be used to construct expression vectors containing sequences encoding NPY-like GPCR polypeptides and appropriate transcriptional and translational control elements. These methods include in vitro recombinant DNA techniques, synthetic techniques, and in vivo genetic recombination. Such techniques are described, for example, in Sambrook et al. (1989)

and in Ausubel et al., CURRENT PROTOCOLS IN MOLECULAR BIOLOGY, John Wiley & Sons, New York, N.Y., 1989.

A variety of expression vector/host systems can be utilized to contain and express sequences encoding an NPY-like GPCR polypeptide. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUE-SCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding an NPY-like GPCR polypeptide, vectors based on SV40 or EBV can be used with an appropriate selectable marker.

Bacterial and Yeast Expression Systems

In bacterial systems, a number of expression vectors can be selected depending upon the use intended for the NPY-like GPCR polypeptide. For example, when a large quantity of an NPY-like GPCR polypeptide is needed for the induction of antibodies, vectors which direct high level expression of fusion proteins that are readily purified can be used. Such vectors include, but are not limited to, multifunctional *E. coli* cloning and expression vectors such as BLUESCRIPT (Stratagene). In a BLUESCRIPT vector, a sequence encoding the NPY-like GPCR polypeptide can be ligated into the vector in frame with sequences for the amino-terminal Met and the subsequent 7 residues of •-galactosidase so that a hybrid protein is produced. pIN vectors (Van Heeke & Schuster, *J. Biol. Chem.* 264, 5503–5509, 1989) or pGEX vectors (Promega, Madison, Wis.) also can be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems can be designed to include heparin, thrombin, or factor Xa protease cleavage sites so that the cloned polypeptide of interest can be released from the GST moiety at will.

In the yeast *Saccharomyces cerevisiae*, a number of vectors containing constitutive or inducible promoters such as alpha factor, alcohol oxidase, and PGH can be used. For reviews, see Ausubel et al. (1989) and Grant et al., *Methods Enzymol.* 153, 516–544, 1987.

Plant and Insect Expression Systems

If plant expression vectors are used, the expression of sequences encoding NPY-like GPCR polypeptides can be driven by any of a number of promoters. For example, viral promoters such as the 35S and 19S promoters of CaMV can be used alone or in combination with the omega leader sequence from TMV (Takamatsu, *EMBO J.* 6, 307–311, 1987). Alternatively, plant promoters such as the small subunit of RUBISCO or heat shock promoters can be used (Coruzzi et al., *EMBO J.* 3, 1671–1680, 1984; Broglie et al., *Science* 224, 838–843, 1984; Winter et al., *Results Probl. Cell Differ.* 17, 85–105, 1991). These constructs can be introduced into plant cells by direct DNA transformation or by pathogen-mediated transfection. Such techniques are described in a number of generally available reviews (e.g., Hobbs or Murray, in MCGRAW HILL YEARBOOK OF SCIENCE AND TECHNOLOGY, McGraw Hill, New York, N.Y., pp. 191–196, 1992).

An insect system also can be used to express an NPY-like GPCR polypeptide. For example, in one such system *Autographa californica* nuclear polyhedrosis virus (AcNPV) is used as a vector to express foreign genes in *Spodoptera frugiperda* cells or in *Trichoplusia* larvae. Sequences encoding NPY-like GPCR polypeptides can be cloned into a non-essential region of the virus, such as the polyhedrin gene, and placed under control of the polyhedrin promoter. Successful insertion of NPY-like GPCR polypeptides will render the polyhedrin gene inactive and produce recombinant virus lacking coat protein. The recombinant viruses can then be used to infect *S. frugiperda* cells or *Trichoplusia* larvae in which NPY-like GPCR polypeptides can be expressed (Engelhard et al., *Proc. Nat. Acad. Sci.* 91, 3224–3227, 1994).

Mammalian Expression Systems

A number of viral-based expression systems can be used to express NPY-like GPCR polypeptides in mammalian host cells. For example, if an adenovirus is used as an expression vector, sequences encoding NPY-like GPCR polypeptides can be ligated into an adenovirus transcription/translation complex comprising the late promoter and tripartite leader sequence. Insertion in a non-essential E1 or E3 region of the viral genome can be used to obtain a viable virus that is capable of expressing an NPY-like GPCR polypeptide in infected host cells (Logan & Shenk, *Proc. Natl. Acad. Sci.* 81, 3655–3659, 1984). If desired, transcription enhancers, such as the Rous sarcoma virus (RSV) enhancer, can be used to increase expression in mammalian host cells.

Human artificial chromosomes (HACs) also can be used to deliver larger fragments of DNA than can be contained and expressed in a plasmid. HACs of 6M to 10M are constructed and delivered to cells via conventional delivery methods (e.g., liposomes, polycationic amino polymers, or vesicles).

Specific initiation signals also can be used to achieve more efficient translation of sequences encoding NPY-like GPCR polypeptides. Such signals include the ATG initiation codon and adjacent sequences. In cases where sequences encoding an NPY-like GPCR polypeptide, its initiation codon, and upstream sequences are inserted into the appropriate expression vector, no additional transcriptional or translational control signals may be needed. However, in cases where only coding sequence, or a fragment thereof, is inserted, exogenous translational control signals (including the ATG initiation codon) should be provided. The initiation codon should be in the correct reading frame to ensure translation of the entire insert. Exogenous translational elements and initiation codons can be of various origins, both natural and synthetic. The efficiency of expression can be enhanced by the inclusion of enhancers that are appropriate for the particular cell system that is used (see Scharf et al., *Results Probl. Cell Differ.* 20, 125–162, 1994).

Host Cells

A host cell strain can be chosen for its ability to modulate the expression of the inserted sequences or to process the expressed NPY-like GPCR polypeptide in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells that have specific cellular machinery and characteristic mechanisms for post-translational activities (e.g., CHO, HeLa, MDCK, HEK293, and WI38), are available from the American Type Culture Collection (ATCC; 10801 University Boulevard, Manassas, Va. 20110-2209) and can be chosen to ensure the correct modification and processing of the foreign protein.

Stable expression is preferred for long-term, high-yield production of recombinant proteins. For example, cell lines which stably express NPY-like GPCR polypeptides can be transformed using expression vectors which can contain viral origins of replication and/or endogenous expression elements and a selectable marker gene on the same or on a separate vector. Following the introduction of the vector, cells can be allowed to grow for 1–2 days in an enriched medium before they are switched to a selective medium. The purpose of the selectable marker is to confer resistance to selection, and its presence allows growth and recovery of cells that successfully express the introduced NPY-like GPCR sequences. Resistant clones of stably transformed cells can be proliferated using tissue culture techniques appropriate to the cell type. See, for example, ANIMAL CELL CULTURE, R. I. Freshney, ed., 1986.

Any number of selection systems can be used to recover transformed cell lines. These include, but are not limited to, the herpes simplex virus thymidine kinase (Wigler et al., *Cell* 11, 223–32, 1977) and adenine phosphoribosyltransferase (Lowy et al., *Cell* 22, 817–23, 1980) genes which can be employed in tk⁻ or aprf⁻ cells, respectively. Also, antimetabolite, antibiotic, or herbicide resistance can be used as the basis for selection. For example, dhfr confers resistance to methotrexate (Wigler et al., *Proc. Natl. Acad. Sci.* 77, 3567–70, 1980), npt confers resistance to the aminoglycosides, neomycin and G-418 (Colbere-Garapin et al., *J. Mol. Biol.* 150, 1–14, 1981), and als and pat confer resistance to chlorsulfuron and phosphinotricin acetyltransferase, respectively (Murray, 1992, supra). Additional selectable genes have been described. For example, trpB allows cells to utilize indole in place of tryptophan, or hisD, which allows cells to utilize histinol in place of histidine (Hartman & Mulligan, *Proc. Natl. Acad. Sci.* 85, 8047–51, 1988). Visible markers such as anthocyanins, •-glucuronidase and its substrate GUS, and luciferase and its substrate luciferin, can be used to identify transformants and to quantify the amount of transient or stable protein expression attributable to a specific vector system (Rhodes et al., *Methods Mol. Biol.* 55, 121–131, 1995).

Detecting Expression of NPY-like GPCR Polypeptides

Although the presence of marker gene expression suggests that the NPY-like GPCR polynucleotide is also present, its presence and expression may need to be confirmed. For example, if a sequence encoding an NPY-like GPCR polypeptide is inserted within a marker gene sequence, transformed cells containing sequences that encode an NPY-like GPCR polypeptide can be identified by the absence of marker gene function. Alternatively, a marker gene can be placed in tandem with a sequence encoding an NPY-like GPCR polypeptide under the control of a single promoter. Expression of the marker gene in response to induction or selection usually indicates expression of the NPY-like GPCR polynucleotide.

Alternatively, host cells which contain an NPY-like GPCR polynucleotide and which express an NPY-like GPCR polypeptide can be identified by a variety of procedures known to those of skill in the art. These procedures include, but are not limited to, DNA—DNA or DNA-RNA hybridizations and protein bioassay or immunoassay techniques which include membrane, solution, or chip-based technologies for the detection and/or quantification of nucleic acid or protein. For example, the presence of a polynucleotide sequence encoding an NPY-like GPCR polypeptide can be detected by DNA-DNA or DNA-RNA hybridization or amplification using probes or fragments or fragments of polynucleotides encoding an NPY-like GPCR polypeptide. Nucleic acid amplification-based assays involve the use of oligonucleotides selected from sequences encoding an NPY-like GPCR polypeptide to detect transformants that contain an NPY-like GPCR polynucleotide.

A variety of protocols for detecting and measuring the expression of an NPY-like GPCR polypeptide, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on an NPY-like GPCR polypeptide can be used, or a competitive binding assay can be employed. These and other assays are described in Hampton et al., SEROLOGICAL METHODS: A LABORATORY MANUAL, APS Press, St. Paul, Minn., 1990) and Maddox et al., *J. Exp. Med.* 158, 1211–1216, 1983).

A wide variety of labels and conjugation techniques are known by those skilled in the art and can be used in various nucleic acid and amino acid assays. Means for producing labeled hybridization or PCR probes for detecting sequences related to polynucleotides encoding NPY-like GPCR polypeptides include oligolabeling, nick translation, end-labeling, or PCR amplification using a labeled nucleotide. Alternatively, sequences encoding an NPY-like GPCR polypeptide can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, magnetic particles, and the like.

Expression and Purification of NPY-like GPCR Polypeptides

Host cells transformed with nucleotide sequences encoding an NPY-like GPCR polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides which encode NPY-like GPCR polypeptides can be designed to contain signal sequences which direct secretion of soluble NPY-like GPCR polypeptides through a prokaryotic or eukaryotic cell membrane or which direct the membrane insertion of membrane-bound NPY-like GPCR polypeptide.

As discussed above, other constructions can be used to join a sequence encoding an NPY-like GPCR polypeptide to a nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). Inclusion of cleavable linker sequences such as those specific for Factor Xa or enterokinase (Invitrogen, San Diego, Calif.) between the purification domain and the NPY-like GPCR polypeptide also can be used to facilitate purification. One such expression vector provides for expression of a fusion protein containing an NPY-like GPCR polypeptide and 6 histidine residues preceding a thioredoxin or an enterokinase cleavage site. The histidine residues facilitate purification by IMAC (immobilized metal ion affinity chromatography, as described in Porath et al., *Prot. Exp. Purif.* 3, 263–281, 1992), while the enterokinase cleavage site provides a means for purifying the NPY-like GPCR polypeptide from the fusion protein. Vectors that contain fusion proteins are disclosed in Kroll et al., *DNA Cell Biol.* 12, 441–453, 1993.

Chemical Synthesis

Sequences encoding an NPY-like GPCR polypeptide can be synthesized, in whole or in part, using chemical methods well known in the art (see Caruthers et al., *Nucl. Acids Res. Symp. Ser.* 215–223, 1980; Horn et al. *Nucl. Acids Res. Symp. Ser.* 225–232, 1980). Alternatively, an NPY-like GPCR polypeptide itself can be produced using chemical methods to synthesize its amino acid sequence, such as by direct peptide synthesis using solid-phase techniques (Merrifield, *J. Am. Chem. Soc.* 85, 2149–2154, 1963; Roberge et al., *Science* 269, 202–204, 1995). Protein synthesis can be performed using manual techniques or by automation. Automated synthesis can be achieved, for example, using Applied Biosystems 431A Peptide Synthesizer (Perkin Elmer). Optionally, fragments of NPY-like GPCR polypeptides can be separately synthesized and combined using chemical methods to produce a full-length molecule.

The newly synthesized peptide can be substantially purified by preparative high performance liquid chromatography (e.g., Creighton, PROTEINS: STRUCTURES AND MOLECULAR PRINCIPLES, W H Freeman and Co., New York, N.Y., 1983). The composition of a synthetic NPY-like GPCR polypeptide can be confirmed by amino acid analysis or sequencing (e.g., the Edman degradation procedure; see Creighton, supra). Additionally, any portion of the amino acid sequence of the NPY-like GPCR polypeptide can be altered during direct synthesis and/or combined using chemical methods with sequences from other proteins to produce a variant polypeptide or a fusion protein.

Production of Altered Polypeptides

As will be understood by those of skill in the art, it may be advantageous to produce NPY-like GPCR polypeptide-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences disclosed herein can be engineered using methods generally known in the art to alter NPY-like GPCR polypeptide-encoding sequences for a variety of reasons, including but not limited to, alterations which modify the cloning, processing, and/or expression of the polypeptide or mRNA product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth.

Antibodies

Any type of antibody known in the art can be generated to bind specifically to an epitope of an NPY-like GPCR polypeptide. "Antibody" as used herein includes intact immunoglobulin molecules, as well as fragments thereof, such as Fab, F(ab')$_2$, and Fv, which are capable of binding an epitope of an NPY-like GPCR polypeptide. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of an NPY-like GPCR polypeptide can be used therapeutically, as well as in immunochemical assays, such as Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody that specifically binds to the immunogen.

Typically, an antibody that specifically binds to an NPY-like GPCR polypeptide provides a detection signal at least 5-, 10-, or 20-fold higher than a detection signal provided with other proteins when used in an immunochemical assay. Preferably, antibodies that specifically bind to NPY-like GPCR polypeptides do not detect other proteins in immunochemical assays and can immunoprecipitate an NPY-like GPCR polypeptide from solution.

NPY-like GPCR polypeptides can be used to immunize a mammal, such as a mouse, rat, rabbit, guinea pig, monkey, or human, to produce polyclonal antibodies. If desired, an NPY-like GPCR polypeptide can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface-active substances (e.g. lysolecithin, pluronic polyols, polyanions, peptides, oil emulsions, keyhole limpet hemocyanin, and dinitrophenol). Among adjuvants used in humans, BCG (*bacilli Calmette-Guerin*) and *Corynebacterium parvum* are especially useful.

Monoclonal antibodies that specifically bind to an NPY-like GPCR polypeptide can be prepared using any technique which provides for the production of antibody molecules by continuous cell lines in culture. These techniques include, but are not limited to, the hybridoma technique, the human B-cell hybridoma technique, and the EBV-hybridoma technique (Kohler et al., *Nature* 256, 495–497, 1985; Kozbor et al., *J. Immunol. Methods* 81, 31–42, 1985; Cote et al., *Proc. Natl. Acad. Sci.* 80, 2026–2030, 1983; Cole et al., *Mol. Cell Biol.* 62, 109–120, 1984).

In addition, techniques developed for the production of "chimeric antibodies," the splicing of mouse antibody genes to human antibody genes to obtain a molecule with appropriate antigen specificity and biological activity, can be used (Morrison et al., *Proc. Natl. Acad. Sci.* 81, 6851–6855, 1984; Neuberger et al., *Nature* 312, 604–608, 1984; Takeda et al., *Nature* 314, 452–454, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions. Alternatively, humanized antibodies can be produced using recombinant methods, as described in GB2188638B. Antibodies that specifically bind to an NPY-like GPCR polypeptide can contain antigen binding sites which are either partially or fully humanized, as disclosed in U.S. Pat. No. 5,565,332.

Alternatively, techniques described for the production of single chain antibodies can be adapted using methods known in the art to produce single chain antibodies that specifically bind to NPY-like GPCR polypeptides. Antibodies with related specificity, but of distinct idiotypic composition, can be generated by chain shuffling from random combinatorial immunoglobin libraries (Burton, *Proc. Natl. Acad. Sci.* 88, 11120–23, 1991).

Single-chain antibodies also can be constructed using a DNA amplification method, such as PCR, using hybridoma cDNA as a template (Thirion et al., 1996, *Eur. J. Cancer Prev.* 5, 507–11). Single-chain antibodies can be mono- or bispecific, and can be bivalent or tetravalent. Construction of tetravalent, bispecific single-chain antibodies is taught, for example, in Coloma & Morrison, 1997, *Nat. Biotechnol.* 15, 159–63. Construction of bivalent, bispecific single-chain antibodies is taught in Mallender & Voss, 1994, *J. Biol. Chem.* 269, 199–206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (Verhaar et al., 1995, *Int. J. Cancer* 61, 497–501; Nicholls et al., 1993, *J. Immunol. Meth.* 165, 81–91).

Antibodies which specifically bind to NPY-like GPCR polypeptides also can be produced by inducing in vivo production in the lymphocyte population or by screening immunoglobulin libraries or panels of highly specific binding reagents as disclosed in the literature (Orlandi et al., *Proc. Natl. Acad. Sci.* 86, 3833–3837, 1989; Winter et al., *Nature* 349, 293–299, 1991).

Other types of antibodies can be constructed and used therapeutically in methods of the invention. For example, chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies according to the invention can be purified by methods well known in the art. For example, antibodies can be affinity purified by passage over a column to which an NPY-like GPCR polypeptide is bound. The bound antibodies can then be eluted from the column using a buffer with a high salt concentration.

Antisense Oligonucleotides

Antisense oligonucleotides are nucleotide sequences that are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of NPY-like GPCR protein gene products in the cell.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, *Meth. Mol. Biol.* 20, 1–8, 1994; Sonveaux, *Meth. Mol. Biol.* 26, 1–72, 1994; Uhlmann et al., *Chem. Rev.* 90, 543–583, 1990.

Modifications of NPY-like GPCR protein gene expression can be obtained by designing antisense oligonucleotides that will form duplexes to the control, 5', or regulatory regions of the NPY-like GPCR protein gene. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature (e.g., Gee et al., in Huber & Carr, MOLECULAR AND IMMUNOLOGIC APPROACHES, Futura Publishing Co., Mt. Kisco, N.Y., 1994). An antisense oligonucleotide also can be designed to block translation of mRNA by preventing the transcript from binding to ribosomes.

Precise complementarity is not required for successful complex formation between an antisense oligonucleotide and the complementary sequence of an NPY-like GPCR polynucleotide. Antisense oligonucleotides which comprise, for example, 2, 3, 4, or 5 or more stretches of contiguous nucleotides which are precisely complementary to an NPY-like GPCR polynucleotide, each separated by a stretch of contiguous nucleotides which are not complementary to adjacent NPY-like GPCR protein nucleotides, can provide sufficient targeting specificity for NPY-like GPCR protein mRNA. Preferably, each stretch of complementary contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular NPY-like GPCR polynucleotide sequence.

Antisense oligonucleotides can be modified without affecting their ability to hybridize to an NPY-like GPCR polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3', 5'-substituted oligonucleotide in which the 3' hydroxyl group or the 5' phosphate group are substituted, also can be employed in a modified antisense oligonucleotide. These modified oligonucleotides can be prepared by methods well known in the art. See, e.g., Agrawal et al., *Trends Biotechnol.* 10, 152–158, 1992; Uhlmann et al., *Chem. Rev.* 90, 543–584, 1990; Uhlmann et al., *Tetrahedron. Lett.* 215, 3539–3542, 1987.

Ribozymes

Ribozymes are RNA molecules with catalytic activity. See, e.g., Cech, *Science* 236, 1532–1539; 1987; Cech, *Ann. Rev. Biochem.* 59, 543–568; 1990, Cech, *Curr. Opin. Struct. Biol.* 2, 605–609; 1992, Couture & Stinchcomb, *Trends Genet.* 12, 510–515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences.

The coding sequence of an NPY-like GPCR polynucleotide, such as the nucleotide sequences shown in SEQ ID NOS:1 and 3, can be used to generate ribozymes which will specifically bind to mRNA transcribed from the NPY-like GPCR polynucleotide. Methods of designing and constructing ribozymes which can cleave other RNA molecules in trans in a highly sequence specific manner have been developed and described in the art (see Haseloff et al. *Nature* 334, 585–591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201).

Specific ribozyme cleavage sites within an NPY-like GPCR protein RNA target can be identified by scanning the target molecule for ribozyme cleavage sites which include the following sequences: GUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate NPY-like GPCR protein RNA targets also can be evaluated by testing accessibility to hybridization with complementary oligonucleotides using ribonuclease protection assays. The nucleotide sequences shown in SEQ ID NOS:1 and 3 and their complements provide a source of suitable hybridization region sequences. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease NPY-like GPCR protein expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, ribozymes can be engineered so that ribozyme expression will occur in response to factors that induce expression of a target gene. Ribozymes also can be engineered to provide an additional level of regulation, so that destruction of mRNA occurs only when both a ribozyme and a target gene are induced in the cells.

Screening Methods

The invention provides assays for screening test compounds that bind to or modulate the activity of an NPY-like GPCR polypeptide or an NPY-like GPCR polynucleotide. A test compound preferably binds to an NPY-like GPCR polypeptide or polynucleotide. More preferably, a test compound decreases or increases the effect of neuropeptide Y or a neuropeptide Y analog as mediated via human NPY-like GPCR protein by at least about 10, preferably about 50, more preferably about 75, 90, or 100% relative to the absence of the test compound.

Test Compounds

Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, *Anticancer Drug Des.* 12, 145, 1997.

Methods for the synthesis of molecular libraries are well known in the art (see, for example, DeWitt et al., *Proc. Natl. Acad. Sci. U.S.A.* 90, 6909, 1993; Erb et al. *Proc. Natl. Acad. Sci. U.S.A.* 91, 11422, 1994; Zuckermann et al., *J. Med. Chem.* 37, 2678, 1994; Cho et al., *Science* 261, 1303, 1993; Carell et al., *Angew. Chem. Int. Ed. Engl.* 33, 2059, 1994; Carell et al., *Angew. Chem. Int. Ed. Engl.* 33, 2061; Gallop et al., *J. Med. Chem.* 37, 1233, 1994). Libraries of compounds can be presented in solution (see, e.g., Houghten, *BioTechniques* 13, 412–421, 1992), or on beads (Lam, *Nature* 354, 82–84, 1991), chips (Fodor, *Nature* 364, 555–556, 1993), bacteria or spores (Ladner, U.S. Pat. No. 5,223,409), plasmids (Cull et al., *Proc. Natl. Acad. Sci. U.S.A.* 89, 1865–1869, 1992), or phage (Scott & Smith, *Science* 249, 386–390, 1990; Devlin, *Science* 249, 404–406, 1990); Cwirla et al., *Proc. Natl. Acad. Sci.* 97, 6378–6382, 1990; Felici, *J. Mol. Biol.* 222, 301–310, 1991; and Ladner, U.S. Pat. No. 5,223,409.

High Throughput Screening

Test compounds can be screened for the ability to bind to NPY-like GPCR polypeptides or polynucleotides or to affect NPY-like GPCR protein activity or NPY-like GPCR protein gene expression using high throughput screening. Using high throughput screening, many discrete compounds can be tested in parallel so that large numbers of test compounds can be quickly screened. The most widely established techniques utilize 96-well microtiter plates. The wells of the microtiter plates typically require assay volumes that range from 50 to 500 µl. In addition to the plates, many instruments, materials, pipettors, robotics, plate washers, and plate readers are commercially available to fit the 96-well format.

Alternatively, "free format assays," or assays that have no physical barrier between samples, can be used. For example, an assay using pigment cells (melanocytes) in a simple homogeneous assay for combinatorial peptide libraries is described by Jayawickreme et al., *Proc. Natl. Acad. Sci. U.S.A.* 19, 1614–18 (1994). The cells are placed under agarose in petri dishes, then beads that carry combinatorial compounds are placed on the surface of the agarose. The combinatorial compounds are partially released the compounds from the beads. Active compounds can be visualized as dark pigment areas because, as the compounds diffuse locally into the gel matrix, the active compounds cause the cells to change colors.

Another example of a free format assay is described by Chelsky, "Strategies for Screening Combinatorial Libraries: Novel and Traditional Approaches," reported at the First Annual Conference of The Society for Biomolecular Screening in Philadelphia, Pa. (Nov. 7–10, 1995). Chelsky placed a simple homogenous enzyme assay for carbonic anhydrase inside an agarose gel such that the enzyme in the gel would cause a color change throughout the gel. Thereafter, beads carrying combinatorial compounds via a photolinker were placed inside the gel and the compounds were partially released by UV-light. Compounds that inhibited the enzyme were observed as local zones of inhibition having less color change.

Yet another example is described by Salmon et al., *Molecular Diversity* 2, 57–63, (1996). In this example, combinatorial libraries were screened for compounds that had cytotoxic effects on cancer cells growing in agar.

Another high throughput screening method is described in Beutel et al., U.S. Pat. No. 5,976,813. In this method, test samples are placed in a porous matrix. One or more solid components are then placed within, on top of, or at the bottom of a matrix such as a gel, a plastic sheet, a filter, or other form of easily manipulated solid support. When samples are introduced to the porous matrix they diffuse sufficiently slowly, such that the assays can be performed without the test samples running together.

Binding Assays

For binding assays, the test compound is preferably a small molecule that binds to and occupies the active site of the NPY-like GPCR polypeptide, thereby making the ligand binding site inaccessible to substrate such that normal biological activity is prevented. Examples of such small molecules include, but are not limited to, small peptides or peptide-like molecules. Potential ligands that bind to a polypeptide of the invention include, but are not limited to, the natural ligands of known NPY-like GPCR proteins and analogues or derivatives thereof. Natural ligands of GPCRs include neuropeptide Y and its analogs.

In binding assays, either the test compound or the NPY-like GPCR polypeptide can comprise a detectable label, such as a fluorescent, radioisotopic, chemiluminescent, or enzymatic label, such as horseradish peroxidase, alkaline phosphatase, or luciferase. Detection of a test compound that is bound to the NPY-like GPCR polypeptide can then be accomplished, for example, by direct counting of radioemmission, by scintillation counting, or by determining conversion of an appropriate substrate to a detectable product.

Alternatively, binding of a test compound to an NPY-like GPCR polypeptide can be determined without labeling either of the interactants. For example, a microphysiometer can be used to detect binding of a test compound with an NPY-like GPCR polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and an NPY-like GPCR polypeptide (McConnell et al., *Science* 257, 1906–1912, 1992).

Determining the ability of a test compound to bind to an NPY-like GPCR polypeptide also can be accomplished using a technology such as real-time Bimolecular Interaction Analysis (BIA) (Sjolander & Urbaniczky, *Anal. Chem.* 63, 2338–2345, 1991, and Szabo et al., *Curr. Opin. Struct. Biol.* 5, 699–705, 1995). BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, an NPY-like GPCR polypeptide can be used as a "bait protein" in a two-hybrid assay or three-hybrid assay (see, e.g., U.S. Pat. No. 5,283,317; Zervos et al., *Cell* 72, 223–232, 1993; Madura et al., *J. Biol. Chem.* 268, 12046–12054, 1993; Bartel et al., *BioTechniques* 14, 920–924, 1993; Iwabuchi et al., *Oncogene* 8, 1693–1696, 1993; and Brent WO94/10300), to identify other proteins which bind to or interact with the NPY-like GPCR polypeptide and modulate its activity.

The two-hybrid system is based on the modular nature of most transcription factors, which consist of separable DNA-binding and activation domains. Briefly, the assay utilizes two different DNA constructs. For example, in one construct, polynucleotide encoding an NPY-like GPCR polypeptide can be fused to a polynucleotide encoding the DNA binding domain of a known transcription factor (e.g., GAL-4). In the other construct a DNA sequence that encodes an unidentified protein ("prey" or "sample") can be fused to a polynucleotide that codes for the activation domain of the known transcription factor. If the "bait" and the "prey" proteins are able to interact in vivo to form an protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein which interacts with the NPY-like GPCR polypeptide.

It may be desirable to immobilize either the NPY-like GPCR polypeptide (or polynucleotide) or the test compound to facilitate separation of bound from unbound forms of one or both of the interactants, as well as to accommodate automation of the assay. Thus, either the NPY-like GPCR polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the NPY-like GPCR polypeptide (or polynucleotide) or test compound to a solid support, including use of covalent and non-covalent linkages, passive absorption, or pairs of binding moieties attached respectively to the polypeptide (or polynucleotide) or test compound and the solid support. Test compounds are preferably bound to the solid support in an array, so that the location of individual test compounds can be tracked. Binding of a test compound to an NPY-like GPCR polypeptide (or polynucleotide) can be accomplished in any vessel suitable for containing the reactants. Examples of such vessels include microtiter plates, test tubes, and microcentrifuge tubes.

In one embodiment, the NPY-like GPCR polypeptide is a fusion protein comprising a domain that allows the NPY-like GPCR polypeptide to be bound to a solid support. For example, glutathione-S-transferase fusion proteins can be adsorbed onto glutathione sepharose beads (Sigma Chemical, St. Louis, Mo.) or glutathione derivatized microtiter plates, which are then combined with the test compound or the test compound and the non-adsorbed NPY-like GPCR polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either an NPY-like GPCR polypeptide (or polynucleotide) or a test compound can be immobilized utilizing conjugation of biotin and streptavidin. Biotinylated NPY-like GPCR polypeptides (or polynucleotides) or test compounds can be prepared from biotin-NHS(N-hydroxysuccinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to an NPY-like GPCR polypeptide, polynucleotide, or a test compound, but which do not interfere with a desired binding site, such as the active site of the NPY-like GPCR polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the NPY-like GPCR polypeptide or test compound, enzyme-linked assays which rely on detecting an activity of the NPY-like GPCR polypeptide, and SDS gel electrophoresis under non-reducing conditions.

Screening for test compounds that bind to an NPY-like GPCR polypeptide or polynucleotide also can be carried out in an intact cell. Any cell that comprises an NPY-like GPCR polypeptide or polynucleotide can be used in a cell-based assay system. An NPY-like GPCR polynucleotide can be naturally occurring in the cell or can be introduced using techniques such as those described above. Binding of the test compound to an NPY-like GPCR polypeptide or polynucleotide is determined as described above.

Functional Assays

Test compounds can be tested for the ability to increase or decrease a biological effect of an NPY-like GPCR polypeptide. Such biological effects can be determined using the functional assays described in the specific examples, below. Functional assays can be carried out after contacting either a purified NPY-like GPCR polypeptide, a cell membrane preparation, or an intact cell with a test compound. A test compound that decreases a functional activity of an NPY-like GPCR protein by at least about 10, preferably about 50, more preferably about 75, 90, or 100% is identified as a potential therapeutic agent for decreasing NPY-like GPCR protein activity. A test compound that increases NPY-like GPCR protein activity by at least about 10, preferably about 50, more preferably about 75, 90, or 100% is identified as a potential therapeutic agent for increasing NPY-like GPCR protein activity.

One such screening procedure involves the use of melanophores that are transfected to express an NPY-like GPCR polypeptide. Such a screening technique is described in WO 92/01810 published Feb. 6, 1992. Thus, for example, such an assay may be employed for screening for a compound which inhibits activation of the receptor polypeptide by contacting the melanophore cells which comprise the receptor with both the receptor ligand (e.g., neuropeptide Y or a neuropeptide Y analog) and a test compound to be screened. Inhibition of the signal generated by the ligand indicates that a test compound is a potential antagonist for the receptor, i.e., inhibits activation of the receptor. The screen may be employed for identifying a test compound that activates the receptor by contacting such cells with compounds to be screened and determining whether each test compound generates a signal, i.e., activates the receptor.

Other screening techniques include the use of cells that express a human NPY-like GPCR polypeptide (for example, transfected CHO cells) in a system that measures extracellular pH changes caused by receptor activation (see, e.g., *Science* 246, 181–296, 1989). For example, test compounds may be contacted with a cell which expresses a human NPY-like GPCR polypeptide and a second messenger response, e.g., signal transduction or pH changes, can be measured to determine whether the test compound activates or inhibits the receptor.

Another such screening technique involves introducing RNA encoding a human NPY-like GPCR polypeptide into *Xenopus* oocytes to transiently express the receptor. The transfected oocytes can then be contacted with the receptor ligand and a test compound to be screened, followed by detection of inhibition or activation of a calcium signal in the case of screening for test compounds that are thought to inhibit activation of the receptor.

Another screening technique involves expressing a human NPY-like GPCR polypeptide in cells in which the receptor is linked to a phospholipase C or D. Such cells include endothelial cells, smooth muscle cells, embryonic kidney cells, etc. The screening may be accomplished as described above by quantifying the degree of activation of the receptor from changes in the phospholipase activity.

Details of functional assays such as those described above are provided in the specific examples, below.

NPY-like GPCR Gene Expression

In another embodiment, test compounds that increase or decrease NPY-like GPCR protein gene expression are identified. An NPY-like GPCR polynucleotide is contacted with a test compound, and the expression of an RNA or polypeptide product of the NPY-like GPCR polynucleotide is determined. The level of expression of appropriate mRNA or polypeptide in the presence of the test compound is compared to the level of expression of mRNA or polypeptide in the absence of the test compound. The test compound can then be identified as a modulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

The level of NPY-like GPCR protein mRNA or polypeptide expression in the cells can be determined by methods well known in the art for detecting mRNA or polypeptide. Either qualitative or quantitative methods can be used. The presence of polypeptide products of an NPY-like GPCR polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into an NPY-like GPCR polypeptide.

Such screening can be carried out either in a cell-free assay system or in an intact cell. Any cell that expresses an NPY-like GPCR polynucleotide can be used in a cell-based assay system. The NPY-like GPCR polynucleotide can be naturally occurring in the cell or can be introduced using techniques such as those described above. Either a primary culture or an established cell line, such as CHO or human embryonic kidney 293 cells, can be used.

Transgenic Animals

The invention also provides transgenic animals bearing human NPY-like GPCR polynucleotides or altered human NPY-like GPCR polynucleotides. Transgenic animals can provide useful model systems for studying the effects of test compounds in the absence of NPY-like GPCR or in the presence of altered forms of the receptor. These animals also can be used to develop therapeutic treatments for diseases associated with alterations in NPY-like GPCR activity (see Therapeutic Indications, below).

The term "transgene" is used herein to describe genetic material that has been or is about to be artificially inserted into the genome of a mammalian cell, particularly a mammalian cell of a living animal. See U.S. Pat. No. 6,060,642. The transgene is used to transform a cell, meaning that a permanent or transient genetic change, preferably a permanent genetic change, is induced in a cell following incorporation of exogenous DNA. A permanent genetic change is generally achieved by introduction of the DNA into the genome of the cell. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc.

Transgenic animals comprise an exogenous nucleic acid sequence present as an extrachromosomal element or stably integrated in all or a portion of its cells, especially in germ cells. Preferably, a transgenic animal comprises stable changes to the germline sequence. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

Transgenic animals fall into two groups, colloquially termed "knockouts" and "knockins." In the present invention, knockouts have a partial or complete loss of function in one or both alleles of an NPY-like GPCR. Knockins have an introduced transgene with altered genetic sequence and function from the endogenous gene. The two may be combined, such that the naturally occurring gene is disabled, and an altered form introduced.

In a knockout, preferably the target gene expression is undetectable or insignificant. A knock-out of an NPY-like GPCR gene means that function of the receptor has been substantially decreased so that expression is not detectable or only present at insignificant levels. This may be achieved by a variety of mechanisms, including introduction of a disruption of the coding sequence, e.g. insertion of one or more stop codons, insertion of a DNA fragment, etc., deletion of coding sequence, substitution of stop codons for coding sequence, etc. In some cases the exogenous transgene sequences are ultimately deleted from the genome, leaving a net change to the native sequence. Different approaches may be used to achieve the "knock-out." A chromosomal deletion of all or part of the native gene may be induced, including deletions of the non-coding regions, particularly the promoter region, 3' regulatory sequences, enhancers, or deletions of gene that activate expression of NPY-like GPCR genes. A functional knock-out may also be achieved by the introduction of an anti-sense construct that blocks expression of the native genes (for example, see Li and Cohen, *Cell* 85, 319–29, 1996). "Knock-outs" also include conditional knock-outs, for example where alteration of the target gene occurs upon exposure of the animal to a substance that promotes target gene alteration, introduction of an enzyme that promotes recombination at the target gene site (e.g. Cre in the Cre-lox system), or other method for directing the target gene alteration postnatally.

A "knock-in" of a target gene means an alteration in a host cell genome that results in altered expression or function of the native NPY-like GPCR gene. Increased (including ectopic) or decreased expression may be achieved by introduction of an additional copy of the target gene, or by operatively inserting a regulatory sequence that provides for enhanced expression of an endogenous copy of the target gene. These changes may be constitutive or conditional, i.e. dependent on the presence of an activator or repressor.

The exogenous gene is usually either from a different species than the animal host, or is otherwise altered in its coding or non-coding sequence. The introduced gene may be a wild-type gene, naturally occurring polymorphism, or a genetically manipulated sequence, for example having deletions, substitutions or insertions in the coding or non-coding regions. The introduced sequence may encode an NPY-like GPCR, or may utilize the NPY-like GPCR promoter operably linked to a reporter gene. Where the introduced gene is a coding sequence, it is usually operably linked to a promoter, which may be constitutive or inducible, and other regulatory sequences required for expression in the host animal. By "operably linked" is meant that a DNA sequence and a regulatory sequence(s) are connected in such a way as to permit gene expression when the appropriate molecules, e.g. transcriptional activator proteins, are bound to the regulatory sequence(s).

Specific constructs of interest, but are not limited to, include anti-sense NPY-like GPCR, which will block native NPY-like GPCR expression, expression of dominant negative NPY-like GPCR mutations, and over-expression of an NPY-like GPCR gene. A detectable marker, such as lacZ may be introduced into the locus, where upregulation of expression will result in an easily detected change in phenotype. Constructs utilizing the NPY-like GPCR promoter region, in combination with a reporter gene or with the coding region, also are of interest.

A series of small deletions and/or substitutions may be made in the NPY-like GPCR gene to determine the role of different exons in DNA binding, transcriptional regulation, etc. By providing expression of NPY-like GPCR protein in cells in which it is otherwise not normally produced, one can induce changes in cell behavior.

DNA constructs for homologous recombination will comprise at least a portion of the NPY-like GPCR gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990) *Methods in Enzymology* 185, 527–37, 1990.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term, and the resulting litters screened for mutant cells having the construct. By providing for a different phenotype of the blastocyst and the ES cells, chimeric progeny can be readily detected.

The chimeric animals are screened for the presence of the modified gene, and males and females having the modification are mated to produce homozygous progeny. If the gene alterations cause lethality at some point in development, tissues or organs can be maintained as allogeneic or congenic grafts or transplants, or in in vitro culture.

Pharmaceutical Compositions

The invention also provides pharmaceutical compositions that can be administered to a patient to achieve a therapeutic effect. Pharmaceutical compositions of the invention can comprise, for example, an NPY-like GPCR polypeptide, NPY-like GPCR polynucleotide, antibodies that specifically bind to an NPY-like GPCR polypeptide, or mimetics, agonists, antagonists, or inhibitors of an NPY-like GPCR polypeptide activity. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically-acceptable carriers comprising excipients and auxiliaries that facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Dragee cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, i.e., dosage.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents that increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee-making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 1–50 mM histidine, 0.1%–2% sucrose, and 2–7% mannitol, at a pH range of 4.5 to 5.5, that is combined with buffer prior to use.

Further details on techniques for formulation and administration can be found in the latest edition of REMINGTON'S PHARMACEUTICAL SCIENCES (Maack Publishing Co., Easton, Pa.). After pharmaceutical compositions have been prepared, they can be placed in an appropriate container and labeled for treatment of an indicated condition. Such labeling would include amount, frequency, and method of administration.

Therapeutic Indications and Methods

GPCRs are ubiquitous in the mammalian host and are responsible for many biological functions, including many pathologies. Accordingly, it is desirable to find compounds and drugs which stimulate a GPCR on the one hand and which can inhibit the function of a GPCR on the other hand. For example, compounds that activate a GPCR may be employed for therapeutic purposes, such as the treatment of asthma, Parkinson's disease, acute heart failure, urinary retention, and osteoporosis. In particular, compounds which activate GPCRs are useful in treating various cardiovascular ailments such as caused by the lack of pulmonary blood flow or hypertension. In addition these compounds may also be used in treating various physiological disorders relating to abnormal control of fluid and electrolyte homeostasis and in diseases associated with abnormal angiotensin-induced aldosterone secretion.

In general, compounds which inhibit activation of a GPCR can be used for a variety of therapeutic purposes, for example, for the treatment of hypotension and/or hypertension, angina pectoris, myocardial infarction, ulcers, asthma, allergies, benign prostatic hypertrophy, and psychotic and neurological disorders including schizophrenia, manic excitement, depression, delirium, dementia or severe mental retardation, dyskinesias, such as Huntington's disease or Tourett's syndrome, among others. Compounds that inhibit GPCRs also are useful in reversing endogenous anorexia, in the control of bulimia, and in treating various cardiovascular ailments such as caused by excessive pulmonary blood flow or hypotension.

Human NPY-like GPCR can be regulated to treat diabetes. Diabetes mellitus is a common metabolic disorder characterized by an abnormal elevation in blood glucose, alterations in lipids and abnormalities (complications) in the cardiovascular system, eye, kidney and nervous system. Diabetes is divided into two separate diseases: type 1 diabetes (juvenile onset), which results from a loss of cells which make and secrete insulin, and type 2 diabetes (adult onset), which is caused by a defect in insulin secretion and a defect in insulin action.

Type 1 diabetes is initiated by an autoimuune reaction that attacks the insulin secreting cells (beta cells) in the pancreatic islets. Agents that prevent this reaction from occurring or that stop the reaction before destruction of the beta cells has been accomplished are potential therapies for this disease. Other agents that induce beta cell proliferation and regeneration also are potential therapies.

Type II diabetes is the most common of the two diabetic conditions (6% of the population). The defect in insulin secretion is an important cause of the diabetic condition and results from an inability of the beta cell to properly detect and respond to rises in blood glucose levels with insulin release. Therapies that increase the response by the beta cell to glucose would offer an important new treatment for this disease.

The defect in insulin action in Type II diabetic subjects is another target for therapeutic intervention. Agents that increase the activity of the insulin receptor in muscle, liver, and fat will cause a decrease in blood glucose and a normalization of plasma lipids. The receptor activity can be increased by agents that directly stimulate the receptor or that increase the intracellular signals from the receptor. Other therapies can directly activate the cellular end process, i.e. glucose transport or various enzyme systems, to generate an insulin-like effect and therefore a produce beneficial outcome. Because overweight subjects have a greater susceptibility to Type II diabetes, any agent that reduces body weight is a possible therapy.

Both Type I and Type diabetes can be treated with agents that mimic insulin action or that treat diabetic complications by reducing blood glucose levels. Likewise, agents that reduces new blood vessel growth can be used to treat the eye complications that develop in both diseases.

Human NPY-like GPCR can be regulated to treat obesity. Obesity and overweight are defined as an excess of body fat relative to lean body mass. An increase in caloric intake or a decrease in energy expenditure or both can bring about this imbalance leading to surplus energy being stored as fat. Obesity is associated with important medical morbidities and an increase in mortality. The causes of obesity are poorly understood and may be due to genetic factors, environmental factors or a combination of the two to cause a positive energy balance. In contrast, anorexia and cachexia are characterized by an imbalance in energy intake versus energy expenditure leading to a negative energy balance and weight loss. Agents that either increase energy expenditure and/or decrease energy intake, absorption or storage would be useful for treating obesity, overweight, and associated comorbidities. Agents that either increase energy intake and/or decrease energy expenditure or increase the amount of lean tissue would be useful for treating cachexia, anorexia and wasting disorders.

This gene, translated proteins and agents which modulate this gene or portions of the gene or its products are useful for treating obesity, overweight, anorexia, cachexia, wasting disorders, appetite suppression, appetite enhancement, increases or decreases in satiety, modulation of body weight, and/or other eating disorders such as bulimia. Also this gene, translated proteins and agents which modulate this gene or portions of the gene or its products are useful for treating obesity/overweight-associated comorbidities including hypertension, type 2 diabetes, coronary artery disease, hyperlipidemia, stroke, gallbladder disease, gout, osteoarthritis, sleep apnea and respiratory problems, some types of cancer including endometrial, breast, prostate, and colon cancer, thrombolic disease, polycystic ovarian syndrome, reduced fertility, complications of pregnancy, menstrual irregularities, hirsutism, stress incontinence, and depression.

This invention further pertains to the use of novel agents identified by the screening assays described above. Accordingly, it is within the scope of this invention to use a test compound identified as described herein in an appropriate animal model. For example, an agent identified as described herein (e.g., a modulating agent, an antisense nucleic acid molecule, a specific antibody, ribozyme, or an NPY-like GPCR polypeptide binding molecule) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

A reagent which affects NPY-like GPCR protein activity can be administered to a human cell, either in vitro or in vivo, to reduce NPY-like GPCR protein activity. The reagent preferably binds to an expression product of a human NPY-like GPCR protein gene. If the expression product is a protein, the reagent is preferably an antibody. For treatment of human cells ex vivo, an antibody can be added to a preparation of stem cells that have been removed from the body. The cells can then be replaced in the same or another human body, with or without clonal propagation, as is known in the art.

In one embodiment, the reagent is delivered using a liposome. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. Preferably, the lipid composition of the liposome is capable of targeting to a specific organ of an animal, such as the lung, liver, spleen, heart brain, lymph nodes, and skin.

A liposome useful in the present invention comprises a lipid composition that is capable of fusing with the plasma membrane of the targeted cell to deliver its contents to the cell. Preferably, the transfection efficiency of a liposome is about 0.5 $\mu$g of DNA per 16 nmole of liposome delivered to about $10^6$ cells, more preferably about 1.0 $\mu$g of DNA per 16 nmole of liposome delivered to about $10^6$ cells, and even more preferably about 2.0 $\mu$g of DNA per 16 nmol of liposome delivered to about $10^6$ cells. Preferably, a liposome is between about 100 and 500 nm, more preferably between about 150 and 450 nm, and even more preferably between about 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a tumor cell, such as a tumor cell ligand exposed on the outer surface of the liposome.

Complexing a liposome with a reagent such as an antisense oligonucleotide or ribozyme can be achieved using methods that are standard in the art (see, for example, U.S. Pat. No. 5,705,151). Preferably, from about 0.1 $\mu$g to about 10 $\mu$g of polynucleotide is combined with about 8 nmol of liposomes, more preferably from about 0.5 $\mu$g to about 5 $\mu$g of polynucleotides are combined with about 8 nmol liposomes, and even more preferably about 1.0 $\mu$g of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. *Trends in Biotechnol.* 11, 202–05 (1993); Chiou et al., GENE THERAPEUTICS: METHODS AND APPLICATIONS OF DIRECT GENE TRANSFER (J. A. Wolff, ed.) (1994); Wu & Wu, *J. Biol. Chem.* 263, 621–24 (1988); Wu et al., *J. Biol. Chem.* 269, 542–46 (1994); Zenke et al., *Proc. Natl. Acad. Sci. U.S.A.* 87, 3655–59 (1990); Wu et al., *J. Biol. Chem.* 266, 338–42 (1991).

Determination of a Therapeutically Effective Dose

The determination of a therapeutically effective dose is well within the capability of those skilled in the art. A therapeutically effective dose refers to that amount of active ingredient that increases or decreases NPY-like GPCR protein activity relative to the NPY-like GPCR protein activity which occurs in the absence of the therapeutically effective dose.

For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions that exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active ingredient or to maintain the desired effect. Factors that can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

If the reagent is a single-chain antibody, polynucleotides encoding the antibody can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Effective in vivo dosages of an antibody are in the range of about 5 μg to about 50 μg/kg, about 50 μg to about 5 mg/kg, about 100 μg to about 500 μg/kg of patient body weight, and about 200 to about 250 μg/kg of patient body weight. For administration of polynucleotides encoding single-chain antibodies, effective in vivo dosages are in the range of about 100 ng to about 200 ng, 500 ng to about 50 mg, about 1 μg to about 2 mg, about 5 μg to about 500 μg, and about 20 μg to about 100 μg of DNA.

If the expression product is mRNA, the reagent is preferably an antisense oligonucleotide or a ribozyme. Polynucleotides that express antisense oligonucleotides or ribozymes can be introduced into cells by a variety of methods, as described above.

Preferably, a reagent reduces expression of an NPY-like GPCR protein gene or the activity of an NPY-like GPCR polypeptide by at least about 10, preferably about 50, more preferably about 75, 90, or 100% relative to the absence of the reagent. The effectiveness of the mechanism chosen to decrease the level of expression of an NPY-like GPCR protein gene or the activity of an NPY-like GPCR polypeptide can be assessed using methods well known in the art, such as hybridization of nucleotide probes to NPY-like GPCR protein-specific mRNA, quantitative RT-PCR, immunologic detection of an NPY-like GPCR polypeptide, or measurement of NPY-like GPCR protein activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects.

Any of the therapeutic methods described above can be applied to any subject in need of such therapy, including, for example, mammals such as dogs, cats, cows, horses, rabbits, monkeys, and most preferably, humans.

Diagnostic Methods

GPCRs also can be used in diagnostic assays for detecting diseases and abnormalities or susceptibility to diseases and abnormalities related to the presence of mutations in the nucleic acid sequences which encode a GPCR. Such diseases, by way of example, are related to cell transformation, such as tumors and cancers, and various cardiovascular disorders, including hypertension and hypotension, as well as diseases arising from abnormal blood flow, abnormal angiotensin-induced aldosterone secretion, and other abnormal control of fluid and electrolyte homeostasis.

Differences can be determined between the cDNA or genomic sequence encoding a GPCR in individuals afflicted with a disease and in normal individuals. If a mutation is observed in some or all of the afflicted individuals but not in normal individuals, then the mutation is likely to be the causative agent of the disease.

Sequence differences between a reference gene and a gene having mutations can be revealed by the direct DNA sequencing method. In addition, cloned DNA segments can be employed as probes to detect specific DNA segments. The sensitivity of this method is greatly enhanced when combined with PCR. For example, a sequencing primer can be used with a double-stranded PCR product or a single-stranded template molecule generated by a modified PCR. The sequence determination is performed by conventional procedures using radiolabeled nucleotides or by automatic sequencing procedures using fluorescent tags.

Genetic testing based on DNA sequence differences can be carried out by detection of alteration in electrophoretic mobility of DNA fragments in gels with or without denaturing agents. Small sequence deletions and insertions can be visualized, for example, by high resolution gel electrophoresis. DNA fragments of different sequences can be distinguished on denaturing formamide gradient gels in which the mobilities of different DNA fragments are retarded in the gel at different positions according to their specific melting or partial melting temperatures (see, e.g., Myers et al., *Science* 230, 1242, 1985). Sequence changes at specific locations can also be revealed by nuclease protection assays, such as RNase and S 1 protection or the chemical cleavage method (e.g., Cotton et al., *Proc. Natl. Acad. Sci. USA* 85, 4397–4401, 1985). Thus, the detection of a specific DNA sequence can be performed by methods such as hybridization, RNase protection, chemical cleavage, direct DNA sequencing or the use of restriction enzymes and Southern blotting of genomic DNA. In addition to direct methods such as gel-electrophoresis and DNA sequencing, mutations can also be detected by in situ analysis.

Altered levels of a GPCR also can be detected in various tissues. Assays used to detect levels of the receptor polypeptides in a body sample, such as blood or a tissue biopsy, derived from a host are well known to those of skill in the art and include radioimmunoassays, competitive binding assays, Western blot analysis, and ELISA assays.

All patents and patent applications cited in this disclosure are expressly incorporated herein by reference. The above disclosure generally describes the present invention. A more complete understanding can be obtained by reference to the following specific examples which are provided for purposes of illustration only and are not intended to limit the scope of the invention.

EXAMPLE 1

Expression of Human NPY-like GPCR cDNA

An RNA blot (Clontech) was probed with radiolabeled human NPY-like GPCR cDNA. The results are shown in FIG. 2. In addition to the abundant 9.5-kb transcript that is highly enriched in brain (B) as compared to kidney (Kd), a major transcript of 4.2-kb can be seen in heart (H) and brain, a 2.6-kb transcript is present in heart, brain and kidney, and a 1.5-kb mRNA can be seen in heart, brain, kidney, and skeletal muscle (SkM). Negligble expression is seen in placenta (Pl), lung (Lu), liver (Li), and pancreas (Pa).

EXAMPLE 2

Comparison of NPY-like GPCR Expression in Obese and Control Rats

Figure 3:
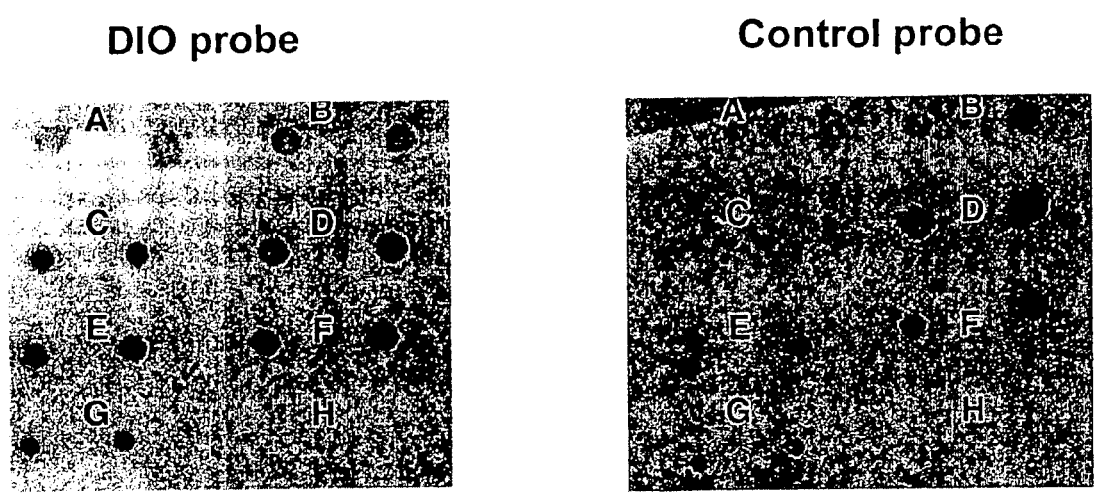
FIG. 3. Reverse-Northern hybridization analysis of radiolabeled hypothalamic cDNA from diet-induced obese and chow-fed rats.

Radiolabeled hypothalamic cDNA from diet-induced obese (DIO) and from chow-fed (Control) rats was hybridized to a dot blot containing cDNAs from eight target genes: (A) β-actin, (B) glyceraldehyde-3-phosphate dehydrogenase (G3PDH), (C) SOCS3, (D) COX1, (E) cathepsin, (F) steroyl CoA desaturase (SCD), (G) novel NPY-like GPCR, and (H) leptin. The expression of the novel NPY-like GPCR, SOCS3, and leptin transcripts is up-regulated in an obese state. The results are shown in FIG. 3.

EXAMPLE 3

Radioligand Binding Assays

Human embryonic kidney 293 cells transfected with a polynucleotide that expresses human NPY-like GPCR are scraped from a culture flask into 5 ml of Tris HCl, 5 mM EDTA, pH 7.5, and lysed by sonication. Cell lysates are centrifuged at 1000 rpm for 5 minutes at 4° C. The supernatant is centrifuged at 30,000×g for 20 minutes at 4° C. The pellet is suspended in binding buffer containing 50 mM Tris HCl, 5 mM MgSO$_4$, 1 mM EDTA, 100 mM NaCl, pH 7.5, supplemented with 0.1% BSA, 2 µg/ml aprotinin, 0.5 mg/ml leupeptin, and 10 µg/ml phosphoramidon. Optimal membrane suspension dilutions, defined as the protein concentration required to bind less than 10% of the added radioligand, are added to 96-well polypropylene microtiter plates containing $^{125}$I-labeled ligand or test compound, non-labeled peptides, and binding buffer to a final volume of 250 µl.

In equilibrium saturation binding assays, membrane preparations are incubated in the presence of increasing concentrations (0.1 nM to 4 nM) of $^{125}$I-labeled ligand or test compound (specific activity 2200 Ci/mmol). The binding affinities of different test compounds are determined in equilibrium competition binding assays, using 0.1 nM $^{125}$I-peptide in the presence of twelve different concentrations of each test compound.

Binding reaction mixtures are incubated for one hour at 30° C. The reaction is stopped by filtration through GF/B filters treated with 0.5% polyethyleneimine, using a cell harvester. Radioactivity is measured by scintillation counting, and data are analyzed by a computerized non-linear regression program.

Non-specific binding is defined as the amount of radioactivity remaining after incubation of membrane protein in the presence of 100 nM of unlabeled peptide. Protein concentration is measured by the Bradford method using Bio-Rad Reagent, with bovine serum albumin as a standard. A test compound which increases the radioactivity of membrane protein by at least 15% relative to radioactivity of membrane protein that was not incubated with a test compound is identified as a compound which binds to a human NPY-like GPCR polypeptide.

EXAMPLE 4

Effect of a Test Compound on Human NPY-like GPCR -mediated Cyclic AMP Formation

Receptor-mediated inhibition of cAMP formation can be assayed in host cells that express human NPY-like GPCR. Cells are plated in 96-well plates and incubated in Dulbecco's phosphate buffered saline (PBS) supplemented with 10 mM HEPES, 5 mM theophylline, 2 µg/ml aprotinin, 0.5 mg/ml leupeptin, and 10 µg/ml phosphoramidon for 20 minutes at 37° C. in 5% CO2. A test compound is added and incubated for an additional 10 minutes at 37° C. The medium is aspirated, and the reaction is stopped by the addition of 100 mM HCl. The plates are stored at 4° C. for 15 minutes. cAMP content in the stopping solution is measured by radioimmunoassay.

Radioactivity is quantified using a gamma counter equipped with data reduction software. A test compound which decreases radioactivity of the contents of a well relative to radioactivity of the contents of a well in the absence of the test compound is identified as a potential inhibitor of cAMP formation. A test compound that increases radioactivity of the contents of a well relative to radioactivity of the contents of a well in the absence of the test compound is identified as a potential enhancer of cAMP formation.

EXAMPLE 5

Effect of a Test Compound on the Mobilization of Intracellular Calcium

Intracellular free calcium concentration can be measured by microspectrofluorometry using the fluorescent indicator dye Fura-2/AM (Bush et al., *J. Neurochem.* 57, 562–74, 1991). Stably transfected cells are seeded onto a 35 mm culture dish containing a glass coverslip insert. Cells are washed with HBS, incubated with a test compound, and loaded with 100 µl of Fura-2/AM (10·M) for 20–40 minutes. After washing with HBS to remove the Fura-2/AM solution, cells are equilibrated in HBS for 10–20 minutes. Cells are then visualized under the 40× objective of a Leitz Fluovert FS microscope.

Fluorescence emission is determined at 510 nM, with excitation wavelengths alternating between 340 nM and 380 nM. Raw fluorescence data are converted to calcium concentrations using standard calcium concentration curves and software analysis techniques. A test compound that increases the fluorescence by at least 15% relative to fluorescence in the absence of a test compound is identified as a compound that mobilizes intracellular calcium.

EXAMPLE 6

Effect of a Test Compound on Phosphoinositide Metabolism

Cells which stably express human NPY-like GPCR cDNA are plated in 96-well plates and grown to confluence. The day before the assay, the growth medium is changed to 100 µl of medium containing 1% serum and 0.5 µCi $^3$H-myinositol. The plates are incubated overnight in a CO$_2$ incubator (5% CO$_2$ at 37° C.). Immediately before the assay, the medium is removed and replaced by 200 µl of PBS containing 10 mM LiCl, and the cells are equilibrated with the new medium for 20 minutes. During this interval, cells also are equilibrated with antagonist, added as a 10 µl aliquot of a 20-fold concentrated solution in PBS.

The $^3$H-inositol phosphate accumulation from inositol phospholipid metabolism is started by adding 10 µl of a solution containing a test compound. To the first well 10 µl are added to measure basal accumulation. Eleven different concentrations of test compound are assayed in the following 11 wells of each plate row. All assays are performed in duplicate by repeating the same additions in two consecutive plate rows.

The plates are incubated in a CO$_2$ incubator for one hour. The reaction is terminated by adding 15 µl of 50% v/v trichloroacetic acid (TCA), followed by a 40 minute incubation at 4° C. After neutralizing TCA with 40 µt of 1 M Tris, the content of the wells is transferred to a Multiscreen HV filter plate (Millipore) containing Dowex AG1-X8 (200–400 mesh, formate form). The filter plates are prepared by adding 200 µl of Dowex AG1-X8 suspension (50% v/v, water:resin) to each well. The filter plates are placed on a vacuum manifold to wash or elute the resin bed. Each well is washed 2 times with 200 µl of water, followed by 2×200 µl of 5 mM sodium tetraborate/60 mM ammonium formate.

The $^3$H-IPs are eluted into empty 96-well plates with 200 µl of 1.2 M ammonium formate/0.1 formic acid. The content of the wells is added to 3 ml of scintillation cocktail, and radioactivity is determined by liquid scintillation counting.

EXAMPLE 7

Receptor Binding Methods

Standard Binding Assays. Binding assays are carried out in a binding buffer containing 50 mM HEPES, pH 7.4, 0.5% BSA, and 5 mM MgCl$_2$. The standard assay for radioligand binding to membrane fragments comprising NPY-like GPCR polypeptides is carried out as follows in 96 well microtiter plates (e.g., Dynatech Immulon II Removawell plates). Radioligand is diluted in binding buffer+PMSF/Baci to the desired cpm per 50 µl, then 50 µl aliquots are added to the wells. For non-specific binding samples, 5 µl of 40 µM cold ligand also is added per well. Binding is initiated by adding 150 µl per well of membrane diluted to the desired concentration (10–30 µg membrane protein/well) in binding buffer+PMSF/Baci. Plates are then covered with Linbro mylar plate sealers (Flow Labs) and placed on a Dynatech Microshaker II. Binding is allowed to proceed at room temperature for 1–2 hours and is stopped by centrifuging the plate for 15 minutes at 2,000×g. The supernatants are decanted, and the membrane pellets are washed once by addition of 200 µl of ice cold binding buffer, brief shaking, and recentrifugation. The individual wells are placed in 12×75 mm tubes and counted in an LKB Gammamaster counter (78% efficiency). Specific binding by this method is identical to that measured when free ligand is removed by rapid (3–5 seconds) filtration and washing on polyethyleneimine-coated glass fiber filters.

Three variations of the standard binding assay are also used.

1. Competitive radioligand binding assays with a concentration range of cold ligand vs. 125I-labeled ligand are carried out as described above with one modification. All dilutions of ligands being assayed are made in 40× PMSF/Baci to a concentration 40× the final concentration in the assay. Samples of peptide (5 µl each) are then added per microtiter well. Membranes and radioligand are diluted in binding buffer without protease inhibitors. Radioligand is added and mixed with cold ligand, and then binding is initiated by addition of membranes.

2. Chemical cross-linking of radioligand with receptor is done after a binding step identical to the standard assay. However, the wash step is done with binding buffer minus BSA to reduce the possibility of non-specific cross-linking of radioligand with BSA. The cross-linking step is carried out as described below.

3. Larger scale binding assays to obtain membrane pellets for studies on solubilization of receptor:ligand complex and for receptor purification are also carried out. These are identical to the standard assays except that (a) binding is carried out in polypropylene tubes in volumes from 1–250 ml, (b) concentration of membrane protein is always 0.5 mg/ml, and (c) for receptor purification, BSA concentration in the binding buffer is reduced to 0.25%, and the wash step is done with binding buffer without BSA, which reduces BSA contamination of the purified receptor.

EXAMPLE 8
Chemical Cross-Linking of Radioligand to Receptor

After a radioligand binding step as described above, membrane pellets are resuspended in 200 µl per microtiter plate well of ice-cold binding buffer without BSA. Then 5 µl per well of 4 mM N-5-azido-2-nitrobenzoyloxysuccinimide (ANB-NOS, Pierce) in DMSO is added and mixed. The samples are held on ice and UV-irradiated for 10 minutes with a Mineralight R-52G lamp (UVP Inc., San Gabriel, Calif.) at a distance of 5–10 cm. Then the samples are transferred to Eppendorf microfuge tubes, the membranes pelleted by centrifugation, supernatants removed, and membranes solubilized in Laemmli SDS sample buffer for polyacrylamide gel electrophoresis (PAGE). PAGE is carried out as described below. Radiolabeled proteins are visualized by autoradiography of the dried gels with Kodak XAR film and DuPont image intensifier screens.

EXAMPLE 8
Membrane Solubilization

Membrane solubilization is carried out in buffer containing 25 mM Tris, pH 8, 10% glycerol (w/v) and 0.2 mM $CaCl_2$ (solubilization buffer). The highly soluble detergents including Triton X-100, deoxycholate, deoxycholate:lysolecithin, CHAPS, and zwittergent are made up in solubilization buffer at 10% concentrations and stored as frozen aliquots. Lysolecithin is made up fresh because of insolubility upon freeze-thawing and digitonin is made fresh at lower concentrations due to its more limited solubility.

To solubilize membranes, washed pellets after the binding step are resuspended free of visible particles by pipetting and vortexing in solubilization buffer at 100,000×g for 30 minutes. The supernatants are removed and held on ice and the pellets are discarded.

EXAMPLE 10
Assay of Solubilized Receptors

After binding of $^{125}I$ ligands and solubilization of the membranes with detergent, the intact R:L complex can be assayed by four different methods. All are carried out on ice or in a cold room at 4–10° C.).

1. Column chromatography (Knuhtsen et al., *Biochem. J.* 254, 641–647, 1988). Sephadex G-50 columns (8×250 mm) are equilibrated with solubilization buffer containing detergent at the concentration used to solubilize membranes and 1 mg/ml bovine serum albumin. Samples of solubilized membranes (0.2–0.5 ml) are applied to the columns and eluted at a flow rate of about 0.7 ml/minute. Samples (0.18 ml) are collected. Radioactivity is determined in a gamma counter. Void volumes of the columns are determined by the elution volume of blue dextran. Radioactivity eluting in the void volume is considered bound to protein. Radioactivity eluting later, at the same volume as free $^{125}I$ ligands, is considered non-bound.

2. Polyethyleneglycol precipitation (Cuatrecasas, *Proc. Natl. Acad. Sci. USA* 69, 318–322, 1972). For a 100 µl sample of solubilized membranes in a 12×75 mm polypropylene tube, 0.5 ml of 1% (w/v) bovine gamma globulin (Sigma) in 0.1 M sodium phosphate buffer is added, followed by 0.5 ml of 25% (w/v) polyethyleneglycol (Sigma) and mixing. The mixture is held on ice for 15 minutes. Then 3 ml of 0.1 M sodium phosphate, pH 7.4, is added per sample. The samples are rapidly (1–3 seconds) filtered over Whatman GF/B glass fiber filters and washed with 4 ml of the phosphate buffer. PEG-precipitated receptor: $^{125}I$-ligand complex is determined by gamma counting of the filters.

3. GFB/PEI filter binding (Bruns et al., *Analytical Biochem.* 132, 74–81, 1983). Whatman GF/B glass fiber filters are soaked in 0.3% polyethyleneimine (PEI, Sigma) for 3 hours. Samples of solubilized membranes (25–100 µl) are replaced in 12×75 mm polypropylene tubes. Then 4 ml of solubilization buffer without detergent is added per sample and the samples are immediately filtered through the GFB/PEI filters (1–3 seconds) and washed with 4 ml of solubilization buffer. CPM of receptor: $^{125}I$-ligand complex adsorbed to filters are determined by gamma counting.

4. Charcoal/Dextran (Paul and Said, *Peptides* 7[*Suppl.* 1], 147–149, 1986). Dextran T70 (0.5 g, Pharmacia) is dissolved in 1 liter of water, then 5 g of activated charcoal (Norit A, alkaline; Fisher Scientific) is added. The suspension is stirred for 10 minutes at room temperature and then stored at 4° C. until use. To measure R:L complex, 4 parts by volume of charcoal/dextran suspension are added to 1 part by volume of solubilized membrane. The samples are mixed and held on ice for 2 minutes and then centrifuged for 2 minutes at 11,000×g in a Beckman microfuge. Free radioligand is adsorbed charcoal/dextran and is discarded with the pellet. Receptor: $^{125}$I-ligand complexes remain in the supernatant and are determined by gamma counting.

EXAMPLE 11

Receptor Purification

Binding of biotinyl-receptor to $GH_4$ Cl membranes is carried out as described above. Incubations are for 1 hour at room temperature. In the standard purification protocol, the binding incubations contain 10 nM Bio-S29. $^{125}$I ligand is added as a tracer at levels of 5,000–100,000 cpm per mg of membrane protein. Control incubations contain 10·M cold ligand to saturate the receptor with non-biotinylated ligand.

Solubilization of receptor:ligand complex also is carried out as described above, with 0.15% deoxycholate:lysolecithin in solubilization buffer containing 0.2 mM $MgCl_2$, to obtain 100,000×g supernatants containing solubilized R:L complex.

Immobilized streptavidin (streptavidin cross-linked to 6% beaded agarose, Pierce Chemical Co.; "SA-agarose") is washed in solubilization buffer and added to the solubilized membranes as ⅓₀ of the final volume. This mixture is incubated with constant stirring by end-over-end rotation for 4–5 hours at 4–10° C. Then the mixture is applied to a column and the non-bound material is washed through. Binding of radioligand to SA-agarose is determined by comparing cpm in the 100,000×g supernatant with that in the column effluent after adsorption to SA-agarose. Finally, the column is washed with 12–15 column volumes of solubilization buffer+0.15% deoxycholate:lysolecithin+1/500 (vol/vol) 100×4pase.

The streptavidin column is eluted with solubilization buffer+0.1 mM EDTA+0.1 mM EGTA+0.1 mM GTP-gamma-S (Sigma)+0.15% (wt/vol) deoxycholate:lysolecithin+1/1000 (vol/vol) 100.times.4pase. First, one column volume of elution buffer is passed through the column and flow is stopped for 20–30 minutes. Then 3–4 more column volumes of elution buffer are passed through. All the eluates are pooled.

Eluates from the streptavidin column are incubated overnight (12–15 hours) with immobilized wheat germ agglutinin (WGA agarose, Vector Labs) to adsorb the receptor via interaction of covalently bound carbohydrate with the WGA lectin. The ratio (vol/vol) of WGA-agarose to streptavidin column eluate is generally 1:400. A range from 1:1000 to 1:200 also can be used. After the binding step, the resin is pelleted by centrifugation, the supernatant is removed and saved, and the resin is washed 3 times (about 2 minutes each) in buffer containing 50 mM HEPES, pH 8, 5 mM $MgCl_2$, and 0.15% deoxycholate:lysolecithin. To elute the WGA-bound receptor, the resin is extracted three times by repeated mixing (vortex mixer on low speed) over a 15–30 minute period on ice, with 3 resin columns each time, of 10 mM N-N'-N"-triacetylchitotriose in the same HEPES buffer used to wash the resin. After each elution step, the resin is centrifuged down and the supernatant is carefully removed, free of WGA-agarose pellets. The three, pooled eluates contain the final, purified receptor. The material non-bound to WGA contain G protein subunits specifically eluted from the streptavidin column, as well as non-specific contaminants. All these fractions are stored frozen at −90° C.

EXAMPLE 12

Identification of Test Compounds that Bind to NPY-like GPCR Polypeptides

Purified NPY-like GPCR polypeptides comprising a glutathione-S-transferase protein and absorbed onto glutathione-derivatized wells of 96-well microtiter plates are contacted with test compounds from a small molecule library at pH 7.0 in a physiological buffer solution. NPY-like GPCR polypeptides comprise an amino acid sequence shown in SEQ ID NO:2. The test compounds comprise a fluorescent tag. The samples are incubated for 5 minutes to one hour. Control samples are incubated in the absence of a test compound.

The buffer solution containing the test compounds is washed from the wells. Binding of a test compound to an NPY-like GPCR polypeptide is detected by fluorescence measurements of the contents of the wells. A test compound that increases the fluorescence in a well by at least 15% relative to fluorescence of a well in which a test compound was not incubated is identified as a compound that binds to an NPY-like GPCR polypeptide.

EXAMPLE 13

Identification of a Test Compound that Decreases NPY-like GPCR Gene Expression

A test compound is administered to a culture of human gastric cells and incubated at 37° C. for 10 to 45 minutes. A culture of the same type of cells incubated for the same time without the test compound provides a negative control.

RNA is isolated from the two cultures as described in Chirgwin et al., Biochem. 18, 5294–99, 1979). Northern blots are prepared using 20 to 30 μg total RNA and hybridized with a $^{32}$P-labeled NPY-like GPCR protein-specific probe at 65° C. in Express-hyb (CLONTECH). The probe comprises at least 11 contiguous nucleotides selected from SEQ ID NO:1. A test compound that decreases the NPY-like GPCR protein-specific signal relative to the signal obtained in the absence of the test compound is identified as an inhibitor of NPY-like GPCR protein gene expression.

EXAMPLE 14

Treatment of Asthma with a Reagent which Specifically Binds to an NPY-like GPCR Gene Product Synthesis of antisense NPY-like GPCR oligonucleotides comprising at least 11 contiguous nucleotides selected from the complement of SEQ ID NOS:1 or 3 is performed on a Pharmacia Gene Assembler series synthesizer using the phosphoramidite procedure (Uhlmann et al., Chem. Rev. 90, 534–83, 1990). Following assembly and deprotection, oligonucleotides are ethanol-precipitated twice, dried, and suspended in phosphate-buffered saline (PBS) at the desired concentration. Purity of these oligonucleotides is tested by capillary gel electrophoreses and ion exchange HPLC. Endotoxin levels in the oligonucleotide preparation are determined using the Limulus Amebocyte Assay (Bang, Biol. Bull. (Woods Hole, Mass.) 105, 361–362, 1953).

The antisense oligonucleotides are administered intra-bronchially to a patient with asthma. The severity of the patient's asthma is lessened.

REFERENCES

1. DeQuidt, M. E. and P. C. Emson, Distribution of neuropeptide Y-like immunoreactivity in the rat central nervous system—II. Immunohistochemical analysis. Neuroscience, 1986. 18(3): p. 545–618.
2. Lundberg, J. M., et al., Co-release of neuropeptide Y and catecholamines during physical exercise in man. Biochem Biophys Res Comrnun, 1985. 133(1): p. 30–6.
3. Morris, M. J., et al., Increases in plasma neuropeptide Y concentrations during sympathetic activation in man. J Auton Nerv Syst, 1986. 17(2): p. 143–9.
4. Pernow, J., Co-release and functional interactions of neuropeptide Y and noradrenaline in peripheral sympathetic vascular control. Acta Physiol Scand Suppl, 1988. 568(1): p. 1–56.
5. Sawchenko, P. E., et al., Colocalization of neuropeptide Y immunoreactivity in brainstem catecholaminergic neurons that project to the paraventricular nucleus of the hypothalamus. J Comp Neurol, 1985. 241(2): p. 138–53.
6. Wahlestedt, C., et al., Norepinephrine and neuropeptide Y: vasoconstrictor cooperation in vivo and in vitro. Am J Physiol, 1990. 258: p. R736–R742.
7. Kaijser, L., et al., Neuropeptide Y is released together with noradrenaline from the human heart during exercise and hypoxia. Clin Physiol, 1990. 10(2): p. 179–88.
8. Lewis, D. E., et al., Intense exercise and food restriction cause similar hypothalamic neuropeptide Y increases in rats. Am J Physiol, 1993. 264: p. E279–E284.
9. McCarthy, H. D., et al., Widespread increases in regional hypothalamic Neuropeptide-Y levels in acute Cold-Exposed rats. Neuroscience, 1993. 54(1): p. 127–132.
10. Zukowska, G. Z. and A. C. Vaz, Role of neuropeptide Y (NPY) in cardiovascular responses to stress. Synapse, 1988. 2(3): p. 293–8.
11. Stanley, B. G., et al., Evidence for neuropeptide Y mediation of eating produced by food deprivation and for a variant of the Y1 receptor mediating this peptide's effect. Peptides, 1992. 13: p. 581–587.
12. Stanley, B. G., Neuropeptide Y in multiple hypothalamic sites controls eating behavior, endocrine, and autonomic systems for body energy balance, in Neuropeptide Y, W. F. Colmers and C. Wahlestedt, Editor. 1993, Humana Press: Totowa, N.J. p. 457–509.
13. Abel, P. W. and C. Han, Effects of neuropeptide Y on contraction, relaxation, and membrane potential of rabbit cerebral arteries. J Cardiovasc Pharmacol, 1989. 13(1): p. 52–63.
14. Han, C. and P. W. Abel, Neuropeptide Y potentiates contraction and inhibits relaxation of rabbit coronary arteries. J Cardiovasc Pharmacol, 1987. 9(6): p. 675–81.
15. Grundemar, L., et al., Biphasic blood pressure response to neuropeptide Y in anesthetized rats. Eur J Pharmacol, 1990. 179(1–2): p. 83–7.
16. Grundemar, L., et al., Characterization of vascular neuropeptide Y receptors. Br J Pharmacol, 1992. 105(1): p. 45–50.
17. Shen, S. H., et al., C-terminal neuropeptide Y fragments are mast cell-dependent vasodepressor agents. Eur. J. Pharmacol., 1993. 204: p. 249–256.
18. Tseng, C. J., et al., Cardiovascular effects of neuropeptide Y in rat brainstem nuclei. Circ Res, 1989. 64(1): p. 55–61.
19. Carter, D. A., M. Vallejo, and S. L. Lightman, Cardiovascular effects of neuropeptide Y in the nucleus tractus solitarius of rats: relationship with noradrenaline and vasopressin. Peptides, 1985. 6(3): p. 421–5.
20. Grundemar, L., C. Wahlestedt, and D. J. Reis, Neuropeptide Y acts at an atypical receptor to evoke cardiovascular depression and to inhibit glutamate responsiveness in the brainstem. J Pharmacol Exp Ther, 1991. 258(2): p. 633–8.
21. Grundemar, L., C. Wahlestedt, and D. J. Reis, Long-lasting inhibition of the cardiovascular responses to glutamate and the baroreceptor reflex elicited by neuropeptide Y injected into the nucleus tractus solitarius of the rat. Neurosci Lett, 1991. 122(1): p. 135–9.
22. Zukowska-Grojec, Z. and C. Wahlestedt, Origin and actions of neuropeptide Y in the cardiovascular system, in Neuropeptide Y, W. F. Colmers and C. Wahlestedt, Editor. 1993, Humana Press: Totowa, N.J. p. 315–388.
23. Edvinsson, L., et al., Congestive heart failure: involvement of perivascular peptides reflecting activity in sympathetic, parasympathetic and afferent fibres. Eur J Clin Invest, 1990. 20(1): p. 85–9.
24. Franco, C. A., et al., Release of neuropeptide Y and noradrenaline from the human heart after aortic occlusion during coronary artery surgery. Cardiovasc Res, 1990. 24(3): p. 242–6.
25. Maisel, A. S., et al., Elevation of plasma neuropeptide Y levels in congestive heart failure. Am J Med, 1989. 86(1): p. 43–8.
26. Wahlestedt, C. and D. J. Reis, Neuropeptide Y-related peptides and their receptors—are the receptors potential therapeutic drug targets? Annu. Rev. Pharmacol. Toxicol., 1993. 32: p.309–352.
27. Wahlestedt, C., S. Regunathan, and D. J. Reis, Identification of cultured cells selectively expressing Y1-, Y2-, or Y3-type receptors for neuropeptide Y/peptide YY. Life Sciences, 1992. 50: p. PL7–PL12.
28. Feth, F., W. Rascher, and M. C. Michel, G-protein coupling and signalling of Y1-like neuropeptide Y receptors in SK-N-MC cells. Naunyn Schmiedebergs Arch Pharmacol, 1991. 344(1): p. 1–7.
29. Motulsky, H. J. and M. C. Michel, Neuropeptide Y mobilizes Ca2+ and inhibits adenylate cyclase in human erythroleukemia cells. Am J Physiol, 1988. 255: p. E880–E885.
30. Wahlestedt, C., et al., Neuropeptide Y receptor subtypes, Y1 and Y2. Ann N Y Acad Sci, 1990. 611(7): p. 7–26.
31. Sahu, A. and S. P. Kalra, Neuropeptidergic regulation of feeding-behavior—neuropeptide-Y. Trends In Endocrinology And Metabolism, 1993. 4(7): p. 217–224.
32. Clark, J. T., et al., Neuropeptide Y and human pancreatic polypeptide stimulate feeding behavior in rats. Endocrinology, 1984. 115(1): p. 427–429.
33. Stanley, B. G. and S. F. Leibowitz, Neuropeptide Y injected in the paraventricular hypothalamus: a powerful stimulant of feeding behavior. Proc. Natl. Acad. Sci. USA, 1985. 82: p. 3940–3943.
34. Stanley, B. G. and S. F. Leibowitz, Neuropeptide Y: stimulation of feeding and drinking by injection into the paraventricular nucleus. Life Sci, 1984. 35(26): p. 2635–42.
35. Zarjevski, N., et al., Chronic intracerebroventricular neuropeptide-Y administration to normal rats mimics hormonal and metabolic changes of obesity. Endocrinology, 1993. 133(4): p. 1753–1758.
36. Billington, C. J. and A. S. Levine, Hypothalamic neuropeptide Y regulation of feeding and energy metabolism. Current Opinion in Neurobiology, 1992. 2: p. 847–851.
37. Leibowitz, S. F., Brain neuropeptide Y: an integrator of endocrine metabolic and behavioral processes. Brain Research Bulletin, 1991. 27: p. 333–337.
38. Billington, C. J., et al., Effects of intracerebroventricular injection of neuropeptide Y on energy metabolism. Am. J. Physiol., 1991. 260: p. R321–R327.
39. Billington, C. J., et al., Neuropeptide-Y in hypothalamic paraventricular nucleus—a center coordinating energy-metabolism. American Journal Of Physiology, 1994. 266 (6): p. R1765–R1770.
40. Kalra, S. P., et al., Neuropeptide Y secretion increases in the paraventricular nucleus in association with increased appetite for food. Proc. Natl. Acad. Sci. USA, 1991. 88: p. 10931–10935.
41. Beck, B., et al., Rapid and localized alterations of neuropeptide Y in discrete hypothalamic nuclei with feeding status. Brain Res, 1990. 528(2): p. 245–9.
42. Brady, L. S., et al., Altered expression of hypothalamic neuropeptide mRNAs in food-restricted and food-deprived rats. Neuroendocrinology, 1990. 52(5): p. 441–7.

43. Calza, L., et al., Increase of neuropeptide Y-like immunoreactivity in the paraventricular nucleus of fasting rats. Neurosci Lett, 1989. 104(1–2): p. 99–104.
44. Sahu, A., P. S. Kalra, and S. P. Kalra, Food deprivation and ingestion induce reciprocal changes in neuropeptide Y concentrations in the paraventricular nucleus. Peptides, 1988. 9(1): p. 83–6.
45. Abe, M., et al., Increased neuropeptide Y content in the arcuatoparaventricular hypothalamic neuronal system in both insulin-dependent and non-insulin-dependent diabetic rats. Brain Res, 1991. 539(2): p. 223–7.
46. Sahu, A., et al., Neuropeptide-Y concentration in microdissected hypothalamic regions and in vitro release from the medial basal hypothalamus-preoptic area of streptozotocin-diabetic rats with and without insulin substitution therapy. Endocrinology, 1990. 126(1): p. 192–8.
47. White, J. D., et al., Increased hypothalamic content of preproneuropeptide-Y messenger ribonucleic acid in streptozotocindiabetic rats. Endocrinology, 1990. 126(2): p. 765–72.
48. Williams, G., et al., Increased hypothalamic neuropeptide Y concentrations in diabetic rat. Diabetes, 1988. 37(6): p. 763–72.
49. Williams, G., et al., Increased neuropeptide Y concentrations in specific hypothalamic regions of streptozocin-induced diabetic rats. Diabetes, 1989. 38(3): p. 321–7.
50. Beck, B., et al., Hypothalamic neuropeptide Y (NPY) in obese Zucker rats: implications in feeding and sexual behaviors. Physiol Behav, 1990. 47(3): p. 449–53.
51. Sanacora, G., et al., Increased hypothalamic content of preproneuropeptide Y messenger ribonucleic acid in genetically obese Zucker rats and its regulation by food deprivation. Endocrinology, 1990. 127(2): p. 730–7.
52. Wahlestedt, C., R. Ekman, and E. Widerlov, Neuropeptide Y (NPY) and the central nervous system: distribution effects and possible relationship to neurological and psychiatric disorders. Prog Neuropsychopharmacol Biol Psychiatry, 1989. 13(1–2): p. 31–54.
53. Larhammar, D., et al., Cloning and functional expression of a human neuropeptide Y/peptide YY receptor of the Y1-type. J. Biol. Chem., 1992. 267: p. 10935–10938.
54. Sheikh, S. P., et al., Localization of Y1 receptors for NPY and PYY on vascular smooth muscle cells in rat pancreas. Am J Physiol, 1991. 260: G250–G257.
55. Wahlestedt, C., N. Yanaihara, and R. Hakanson, Evidence for different pre- and post-junctional receptors for neuropeptide Y and related peptides. Regul Pept, 1986. 13(3–4): p. 307–18.
56. Jorgensen, J. C., J. Fuhlendorff, and T. W. Schwartz, Structure-function studies on neuropeptide Y and pancreatic polypeptide—evidence for two PP-fold receptors in vas deferens. Eur J Pharmacol, 1990. 186(1): p. 105–14.
57. Cox, H. M. and J. L. Krstenansky, The effects of selective amino acid substitution upon neuropeptide Y antisecretory potency in rat jejunum mucosa. Peptides, 1991. 12(2): p. 323–7.
58. Aicher, S. A., et al., Receptol—selective analogs demonstrate NPY/PYY receptor heterogeneity in rat brain. Neurosci Lett, 1991. 130(1): p. 32–6.
59. Balasubramaniam, A., et al., Characterization of neuropeptide Y binding sites in rat cardiac ventricular membranes. Peptides, 1990. 11(3): p. 545–50.
60. Li, X. J., et al., Cloning, functional expression, and developmental regulation of a neuropeptide Y receptor from Drosophila melanogaster. J Biol Chem, 1992. 267 (1): p. 9–12.
61. Roman, F. J., et al., Neuropeptide Y and peptide YY interact with rat brain sigma and PCP binding sites. Eur J Pharmacol, 1989. 174(2–3): p. 301–2.
62. Schwartz, T. W., S. P. Sheikh, and M. M. O'Hare, Receptors on phaeochromocytoma cells for two members of the PP-fold family—NPY and PP. Febs Lett, 1987. 225(1–2): p. 209–14.
63. Schwartz, T. W., et al., Signal epitopes in the three-dimensional structure of neuropeptide Y. Interaction with Y1, Y2, and pancreatic polypeptide receptors. Ann N Y Acad Sci, 1990. 611(35): p. 35–47.
64. Wahlestedt, C., et al., Modulation of anxiety and neuropeptide Y-Y1 receptors by antisense oligodeoxynucleotides. Science, 1993. 259: p. 528–531.
65. Jolicoeur, F. B., et al., In vivo structure activity study supports the existence of heterogeneous neuropeptide Y receptors. Brain Res Bull, 1991. 26(2): p. 309–11.
66. Leibowitz, S. F. and J. T. Alexander, Analysis of neuropeptide Y-induced feeding: dissociation of Y1 and Y2 receptor effects on natural meal patterns. Peptides, 1991. 12(6): p. 1251–60.
67. Inui, A., et al., Characterization of peptide YY receptors in the brain. Endocrinology, 1999. 124(1): p. 402–9.
68. Boublik, J., et al., Neuropeptide Y and neuropeptide Y18–36. Structural and biological characterization. Int J Pept Protein Res, 1989. 33(1): p. 11–5.
69. Eva, C., et al., Molecular cloning of a novel G protein-coupled receptor that may belong to the neuropeptide receptor family. FEBS Lett., 1990. 271: p. 91–84.
70. Herzog, H., et al., Cloned human neuropeptide Y receptor couples to two different second messenger systems. Proc Natl Acad Sci U S A, 1992. 89: p. 5794–5798.
71. Rose, P., et al., Cloning and functional expression of a cDNA encoding a human type 2 Neuropeptide Y receptor. J Biol Chem 1995. 270: p. 22661–22664.
72. Gerald, C., et al., Expression cloning and pharmacological characterization of a human hippocampal neuropeptide Y/peptide YY Y2 receptor subtype. J Biol Chem 1995. 270: p. 26758–26761.
73. Lundell, I. et al., Cloning of a human receptor of the NPY receptor family with high affinity for pancreatic polypeptide and peptide YY. J Biol Chem 1995. 270: p. 29123–29128.
74. Bard, J., et al., Cloning and functional expression of a human Y4 subtype receptor for pancreatic polypeptide, neuropeptide Y, and peptide YY. J Biol Chem 1995. 270: p. 26762–26765.

Attachment 1

```
BLAST 2 SEQUENCES RESULTS
Query: SEQ ID NO:1 of Ser. No. 60/216,523
Subject: SEQ ID NO:1 of Ser. No. 09/899,532

Score = 3288 bits (1710), Expect = 0.0
Identities = 1710/1710 (100%)
Strand = Plus / Plus
```

-continued

```
Query:    1 tggccctcgaggccaagaattcggcacgaggaggcgggagccagaggcgccaggaccct    60
            ||||||||||||||||||||||||||||||||||||||||||||||||||||||||||||
Sbjct:    1 tggccctcgaggccaagaattcggcacgaggaggcgggagccagaggcgccaggaccct    60

Query:   61 cgcgtggcgctccagcaccccagaccgtggcggcgcctcgccttagggaagagcaaggga   120
            ||||||||||||||||||||||||||||||||||||||||||||||||||||||||||||
Sbjct:   61 cgcgtggcgctccagcaccccagaccgtggcggcgcctcgccttagggaagagcaaggga   120

Query:  121 agaactttatttgaaccgcgaacattttttggtcactgagatcgagtctcccagtgcttt   180
            ||||||||||||||||||||||||||||||||||||||||||||||||||||||||||||
Sbjct:  121 agaactttatttgaaccgcgaacattttttggtcactgagatcgagtctcccagtgcttt   180

Query:  181 ggcttcccgcctctttatcgtgggtttgatccctgagctgctctccttcccgaacctcc   240
            ||||||||||||||||||||||||||||||||||||||||||||||||||||||||||||
Sbjct:  181 ggcttcccgcctctttatcgtgggtttgatccctgagctgctctccttcccgaacctcc   240

Query:  241 cggggtgcagcctagagcccteccgcgcggctgactccagagtagaggaagggaggcggc   300
            ||||||||||||||||||||||||||||||||||||||||||||||||||||||||||||
Sbjct:  241 cggggtgcagcctagagcccteccgcgcggctgactccagagtagaggaagggaggcggc   300

Query:  301 ctccggctggtcccccgaagccctcgctgccccgcagatgcggatggccagccagtagcg   360
            ||||||||||||||||||||||||||||||||||||||||||||||||||||||||||||
Sbjct:  301 ctccggctggtcccccgaagccctcgctgccccgcagatgcggatggccagccagtagcg   360

Query:  361 ggcggtggccccgcgtcccgggagcgcacagcaatgcaggcgcttaacattaccccggag   420
            ||||||||||||||||||||||||||||||||||||||||||||||||||||||||||||
Sbjct:  361 ggcggtggccccgcgtcccgggagcgcacagcaatgcaggcgcttaacattaccccggag   420

Qyery:  421 cagttctctcggctgctgcgggaccacaacctgacgcgggagcagttcatcgctctgtac   480
            ||||||||||||||||||||||||||||||||||||||||||||||||||||||||||||
Sbjct:  421 cagttctctcggctgctgcgggaccacaacctgacgcgggagcagttcatcgctctgtac   480

Query:  481 cggctgcgaccgctcgtctacaccccagagctgccgggacgcgccaagctggccctcgtg   540
            ||||||||||||||||||||||||||||||||||||||||||||||||||||||||||||
Sbjct:  481 cggctgcgaccgctcgtctacaccccagagctgccgggacgcgccaagctggccctcgtg   540

Query:  541 ctcaccggcgtgctcatcttcgccctggcgctctttggcaatgctctggtgttctacgtg   600
            ||||||||||||||||||||||||||||||||||||||||||||||||||||||||||||
Sbjct:  541 ctcaccggcgtgctcatcttcgccctggcgctctttggcaatgctctggtgttctacgtg   600

Query:  601 gtgacccgcagcaaggccatgcgcaccgtcaccaacatctttatctgctccttggcgctc   660
            ||||||||||||||||||||||||||||||||||||||||||||||||||||||||||||
Sbjct:  601 gtgacccgcagcaaggccatgcgcaccgtcaccaacatctttatctgctcattggcgatc   660

Query:  661 agtgacctgctcatcaccttcttctgcattcccgtcaccatgctccagaacatttccgac   720
            ||||||||||||||||||||||||||||||||||||||||||||||||||||||||||||
Sbjct:  661 agtgacctgctcatcaccttcttctgcattcccgtcaccatgctccagaacatttccgac   720

Query:  721 aactggctgggggtgctttcatttgcaagatggtgccatttgtccagtctaccgctgtt   780
            ||||||||||||||||||||||||||||||||||||||||||||||||||||||||||||
Sbjct:  721 aactggctgggggtgctttcatttgcaagatggtgccatttgtccagtctaccgctgtt   780

Query:  781 gtgacagaaatcctcactatgacctgcattgctgtggaaaggcaccagggacttgtgcat   840
            ||||||||||||||||||||||||||||||||||||||||||||||||||||||||||||
Sbjct:  781 gtgacagaaatcctcactatgacctgcattgctgtggaaaggcaccagggacttgtgcat   840

Query:  841 ccttttaaaatgaagtggcaatacaccaaccgaagggctttcacaatgctaggtgtggtc   900
            ||||||||||||||||||||||||||||||||||||||||||||||||||||||||||||
Sbjct:  841 ccttttaaaatgaagtggcaatacaccaaccgaagggctttcacaatgctaggtgtggtc   900

Query:  901 tggctggtggcagtcatcgtaggatcacccatgtggcacgtgcaacaacttgagatcaaa   960
            ||||||||||||||||||||||||||||||||||||||||||||||||||||||||||||
Sbjct:  901 tggctggtggcagtcatcgtaggatcacccatgtggcacgtgcaacaacttgagatcaaa   960

Query:  961 tatgacttcctatatgaaaaggaacacatctgctgcttagaagagtggaccagccctgtg  1020
            ||||||||||||||||||||||||||||||||||||||||||||||||||||||||||||
Sbjct:  961 tatgacttcctatatgaaaaggaacacatctgctgcttagaagagtggaccagccctgtg  1020

Query: 1021 caccagaagatctacaccaccttcatccttgtcatcctcttcctcctgcctcttatggtg  1080
            ||||||||||||||||||||||||||||||||||||||||||||||||||||||||||||
Sbjct: 1021 caccagaagatctacaccaccttcatccttgtcatcctcttcctcctgcctcttatggtg  1080

Query: 1081 atgcttattctgtacagtaaaattggttatgaactttggataaagaaaagagttggggat  1140
            ||||||||||||||||||||||||||||||||||||||||||||||||||||||||||||
Sbjct: 1081 atgcttattctgtacagtaaaattggttatgaactttggataaagaaaagagttggggat  1140

Query: 1141 ggttcagtgcttcgaactattcatggaaaagaaatgtccaaaatagccaggaagaagaaa  1200
            ||||||||||||||||||||||||||||||||||||||||||||||||||||||||||||
Sbjct: 1141 ggttcagtgcttcgaactattcatggaaaagaaatgtccaaaatagccaggaagaagaaa  1200
```

```
                                      -continued
Query:  1201  cgagctgtcattatgatggtgacagtggtggctctctttgctgtgtgctgggcaccattc  1260
              ||||||||||||||||||||||||||||||||||||||||||||||||||||||||||||
Sbjct:  1201  cgagctgtcattatgatggtgacagtggtggctctctttgctgtgtgctgggcaccattc  1260

Query:  1261  catgttgtccatatgatgattgaatacagtaattttgaaaaggaatatgatgatgtcaca  1320
              ||||||||||||||||||||||||||||||||||||||||||||||||||||||||||||
Sbjct:  1261  catgttgtccatatgatgattgaatacagtaattttgaaaaggaatatgatgatgtcaca  1320

Query:  1321  atcaagatgattttgctatcgtgcaaattattggattttccaactccatctgtaatccc   1380
              ||||||||||||||||||||||||||||||||||||||||||||||||||||||||||||
Sbjct:  1321  atcaagatgattttgctatcgtgcaaattattggattttccaactccatctgtaatccc   1380

Query:  1381  attgtctatgcatttatgaatgaaaacttcaaaaaaaatgttttgtctgcagtttgttat   1440
              ||||||||||||||||||||||||||||||||||||||||||||||||||||||||||||
Sbjct:  1381  attgtctatgcatttatgaatgaaaacttcaaaaaaaatgttttgtctgcagtttgttat   1440

Query:  1441  tgcatagtaaataaaaccttctctccagcacaaaggcatggaaattcaggaattacaatg   1500
              ||||||||||||||||||||||||||||||||||||||||||||||||||||||||||||
Sbjct:  1441  tgcatagtaaataaaaccttctctccagcacaaaggcatggaaattcaggaattacaatg   1500

Query:  1501  atgcggaagaaagcaaagttttccctcagagagaatccagtggaggaaaccaaaggagaa   1560
              ||||||||||||||||||||||||||||||||||||||||||||||||||||||||||||
Sbjct:  1501: atgcggaagaaagcaaagttttccctcagagagaatccagtggaggaaaccaaaggagaa   1560

Query:  1561  gcattcagtgatggcaacattgaagtcaaattgtgtgaacagacagaggagaagaaaaag   1620
              ||||||||||||||||||||||||||||||||||||||||||||||||||||||||||||
Sbjct:  1561  gcattcagtgatggcaacattgaagtcaaattgtgtgaacagacagaggagaagaaaaag   1620

Query:  1621  ctcaaacgacatcttgctctctttaggtctgaactggctgagaattctcctttagacagt   1680
              ||||||||||||||||||||||||||||||||||||||||||||||||||||||||||||
Sbjct:  1621  ctcaaacgacatcttgctctctttaggtctgaactggctgagaattctcctttagacagt   1680

Query:  1681  gggcattaattataacaatatcttcataat                                1710
              ||||||||||||||||||||||||||||||
Sbjct:  1681  gggcattaattataacaatatcttcataat                                1710
```

Attachment 2

BLAST 2 SEQUENCES RESULTS
Query: SEQ ID NO:2 of Ser. No. 60/216,523
Subject: SEQ ID NO:2 of Ser. No. 09/899,532

Score = 856 bits (2235), Expect = 0.0
Identities = 431/431 (100%), Positives 431/431 (100%)

```
Query:   1   MQALNITPEQFSRLLRDHNLTREQFIALYRLRPLVYTPELPGRAKLALVLTGVLIFALAL   60
             MQALNITPEQFSRLLRDHNLTREQFIALYRLRPLVYTPELPGRAKLALVLTGVLIFALAL
Sbjct:   1   MQALNITPEQFSRLLRDHNLTREQFIALYRLRPLVYTPELPGRAKLALVLTGVLIFALAL   60

Query:  61   FGNALVFYVVTRSKAMRTVTNIFICSLALSDLLITFFCIPVTMLQNISDNWLGGAFICKM  120
             FGNALVFYVVTRSKAMRTVTNIFICSLALSDLLITFFCIPVTMLQNISDNWLGGAFICKM
Sbjct:  61   FGNALVFYVVTRSKAMRTVTNIFICSLALSDLLITFFCIPVTMLQNISDNWLGGAFICKM  120

Query: 121   VPFVQSTAVVTEILTMTCIAVERHQGLVHPFKMKWQYTNRRAFTMLGVVWLVAVIVGSPM  180
             VPFVQSTAVVTEILTMTCIAVERHQGLVHPFKMKWQYTNRRAFTMLGVVWLVAVIVGSPM
Sbjct: 121   VPFVQSTAVVTEILTMTCIAVERHQGLVHPFKMKWQYTNRRAFTMLGVVWLVAVIVGSPM  180

Query: 181   WHVQQLEIKYDFLYEKEHICCLEEWTSPVHQKIYTTFILVILFLLPLMVMLILYSKIGYE  240
             WHVQQLEIKYDFLYEKEHICCLEEWTSPVHQKIYTTFILVILFLLPLMVMLILYSKIGYE
Sbjct: 181   WHVQQLEIKYDFLYEKEHICCLEEWTSPVHQKIYTTFILVILFLLPLMVMLILYSKIGYE  240

Query: 241   LWIKKRVGDGSVLRTIHGKEMSKIARKKKRAVIMMVTVVALFAVCWAPFHVVHMMIEYSN  300
             LWIKKRVGDGSVLRTIHGKEMSKIARKKKRAVIMMVTVVALFAVCWAPFHVVHMMIEYSN
Sbjct: 241   LWIKKRVGDGSVLRTIHGKEMSKIARKKKRAVIMMVTVVALFAVCWAPFHVVHMMIEYSN  300

Query: 301   FEKEYDDVTIKMIFAIVQIIGFSNSICNPIVYAFMNENFKKNVLSAVCYCIVNKTFSPAQ  360
             FEKEYDDVTIKMIFAIVQIIGFSNSICNPIVYAFMNENFKKNVLSAVCYCIVNKTFSPAQ
Sbjct: 301   FEKEYDDVTIKMIFAIVQIIGFSNSICNPIVYAFMNENFKKNVLSAVCYCIVNKTFSPAQ  360

Query: 361   RHGNSGITMMRKKAKFSLRENPVEETKGEAFSDGNIEVKLCEQTEEKKKLKRHLALFRSE  420
             RHGNSGITMMRKKAKFSLRENPVEETKGEAFSDGNIEVKLCEQTEEKKKLKRHLALFRSE
Sbjct: 361   RHGNSGITMMRKKAKFSLRENPVEETKGEAFSDGNIEVKLCEQTEEKKKLKRHLALFRSE  420

Query: 421   LAENSPLDSGH                                                  431
             LAENSPLDSGH
Sbjct: 421   LAENSPLDSGH                                                  431
```

What is claimed is:

1. An isolated polynucleotide encoding a polypeptide that comprises the amino acid sequence shown in SEQ ID NO:2.

2. The isolated polynucleotide of claim 1 which comprises the nucleotide sequence shown in SEQ ID NO:1.

3. The isolated polynucleotide of claim 1 which consists of the nucleotide sequence shown in SEQ ID NO:1.

4. The isolated polynucleotide of claim 1 which is a cDNA molecule.

5. An expression vector comprising a polynucleotide that encodes a polypeptide comprising the amino acid sequence shown in SEQ ID NO:2.

6. The expression vector of claim 5 which comprises the nucleotide sequence shown in SEQ ID NO:1.

7. A host cell comprising an expression vector comprising a polynucleotide that encodes a polypeptide comprising the amino acid sequence shown in SEQ ID NO:2.

8. The host cell of claim 7 wherein the expression vector comprises the nucleotide sequence shown in SEQ ID NO:1.

9. A method of producing a polypeptide comprising the amino acid sequence shown in SEQ ID NO:2, comprising the steps of: culturing a host cell comprising an expression vector that comprises the nucleotide sequence shown in SEQ ID NO:1 under conditions whereby the polypeptide is expressed; and isolating the polypeptide.

* * * * *